US011633361B2

(12) United States Patent
Dixit et al.

(10) Patent No.: US 11,633,361 B2
(45) Date of Patent: *Apr. 25, 2023

(54) SOFT CHEW PHARMACEUTICAL FORMULATIONS

(71) Applicant: First Time US Generics LLC, Broomall, PA (US)

(72) Inventors: Manesh A. Dixit, Broomall, PA (US); Vaibhav L. Pawar, Broomall, PA (US); Rushi R. Patel, Broomall, PA (US); Mineshkumar D. Patel, Broomall, PA (US); Amol Somwanshi, Navi Mumbai (IN)

(73) Assignee: First Time US Generics LLC, Broomall, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/894,514

(22) Filed: Jun. 5, 2020

(65) Prior Publication Data

US 2020/0297643 A1 Sep. 24, 2020

Related U.S. Application Data

(63) Continuation of application No. 16/140,477, filed on Sep. 24, 2018, now abandoned, which is a continuation-in-part of application No. 15/629,354, filed on Jun. 21, 2017, now Pat. No. 10,117,831, which is a continuation-in-part of application No. PCT/US2016/067443, filed on Dec. 19, 2016.

(60) Provisional application No. 62/269,951, filed on Dec. 19, 2015.

(51) Int. Cl.
| | |
|---|---|
| *A61K 9/20* | (2006.01) |
| *A61K 31/5395* | (2006.01) |
| *A61K 31/167* | (2006.01) |
| *A61K 31/403* | (2006.01) |
| *A61K 31/546* | (2006.01) |
| *A61K 31/415* | (2006.01) |
| *A61K 31/496* | (2006.01) |
| *A61K 31/192* | (2006.01) |
| *A61K 31/501* | (2006.01) |
| *A61K 9/00* | (2006.01) |

(52) U.S. Cl.
CPC .......... *A61K 9/2095* (2013.01); *A61K 9/0056* (2013.01); *A61K 9/2009* (2013.01); *A61K 9/2018* (2013.01); *A61K 9/2054* (2013.01); *A61K 9/2059* (2013.01); *A61K 9/2068* (2013.01); *A61K 9/2081* (2013.01); *A61K 31/167* (2013.01); *A61K 31/192* (2013.01); *A61K 31/403* (2013.01); *A61K 31/415* (2013.01); *A61K 31/496* (2013.01); *A61K 31/501* (2013.01); *A61K 31/5395* (2013.01); *A61K 31/546* (2013.01)

(58) Field of Classification Search
CPC ................ A61K 9/2095; A61K 9/0056; A61K 9/2009; A61K 9/2018; A61K 9/2054; A61K 9/2059; A61K 9/2068; A61K 9/2081; A61K 31/167; A61K 31/192; A61K 31/403; A61K 31/415; A61K 31/496; A61K 31/501; A61K 31/5395; A61K 31/546

See application file for complete search history.

(56) References Cited

U.S. PATENT DOCUMENTS

| | | |
|---|---|---|
| 4,327,076 A | 4/1982 | Puglia |
| 4,327,077 A | 4/1982 | Puglia |
| 4,582,709 A | 4/1986 | Peters |
| 4,882,161 A | 11/1989 | Scheurer |
| 5,380,535 A | 1/1995 | Geyer |
| 5,576,014 A | 11/1996 | Mizumoto |
| 5,599,577 A | 2/1997 | Stevens |
| 5,637,313 A | 6/1997 | Chau |
| 5,679,376 A | 10/1997 | Stevens |
| 5,817,340 A | 10/1998 | Roche |
| 5,840,334 A | 11/1998 | Raiden |

(Continued)

FOREIGN PATENT DOCUMENTS

| | | |
|---|---|---|
| EP | 1924151 B1 | 5/2008 |
| WO | 93/13758 A1 | 7/1993 |

(Continued)

OTHER PUBLICATIONS

Fred A. Rowley, Compressing Force: Myth vs Reality, Pharmaceutical Manufacturing, Jan. 10, 2018 https://www.pharmamanufacturing.com/articles/2008/005/ (checked Sep. 5, 2019).

Patent Cooperation Treaty, Written Opinion of International Search Authority, Application PCT/US2016/067443, dated Mar. 27, 2017.

Patent Cooperation Treaty, International Search Report, Application PCT/US2016/067443, dated Mar. 27, 2017.

Patent Cooperation Treaty, Applicant's Informal Comments Under §7.030 of the PCT Applicant's Guide on the Written Opinion of the International Search Authority, Application PCT/US2016/067443, dated May 28, 2017.

(Continued)

*Primary Examiner* — Robert A Wax
*Assistant Examiner* — Olga V. Tcherkasskaya
(74) *Attorney, Agent, or Firm* — West Law Office LLC

(57) ABSTRACT

A product and process of manufacturing an edible soft-chewable dosage form for the delivery of pharmaceutically active ingredients or nutritional agents orally to an animal or human subject, by forming a granulated soft-chew mass by appropriate mixing and sifting steps, and forming tablets with a compression press. Such soft-chew dosage forms have hardness of less than about two kilopond (2 kp) and friability of less than about one percent (1%) at three-hundred (300) rotations when measured according to the United States Pharmacopeia (USP) test. The process for manufacturing such compressed soft-chew tablets employs compression (tablet) pressing equipment to produce soft-chew tablets of consistent weight and texture.

8 Claims, 4 Drawing Sheets

(56) References Cited

U.S. PATENT DOCUMENTS

Figure 1:
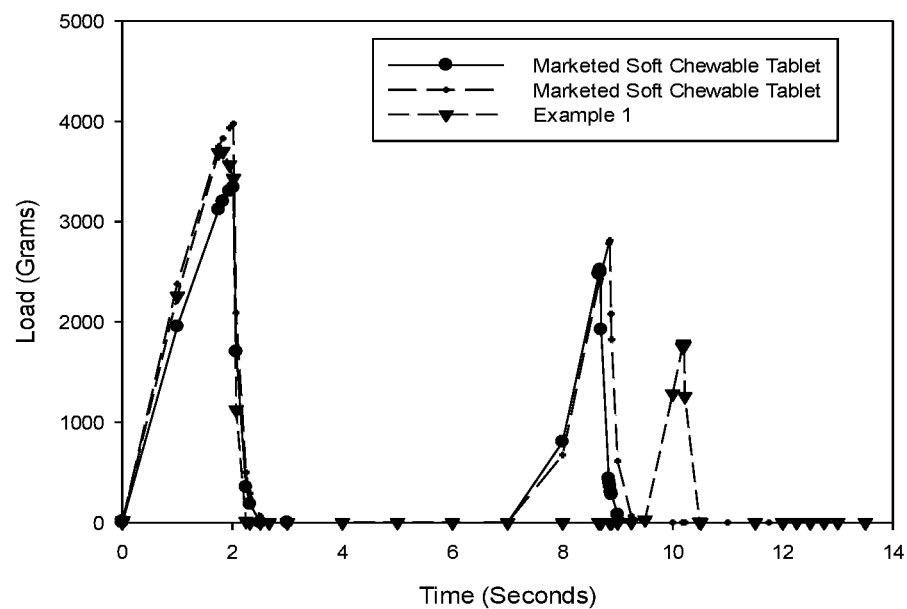

| | | |
|---|---|---|
| 5,853,758 A | 12/1998 | Lo |
| 6,270,790 B1 | 8/2001 | Robinson |
| 6,432,442 B1 | 8/2002 | Buchler |
| 6,471,991 B2 | 10/2002 | Robinson |
| 6,495,177 B1 | 12/2002 | deVries |
| 6,517,886 B1 | 2/2003 | Chau |
| 6,814,978 B2 | 11/2004 | Bunick |
| 7,029,699 B2 | 4/2006 | Robinson |
| 7,914,811 B2 | 3/2011 | Bunick |
| 7,955,632 B2 | 6/2011 | Paulsen |
| 8,124,124 B2 * | 2/2012 | Sherry ............... A61P 19/02 424/464 |
| 8,114,455 B2 | 10/2012 | Paulsen |
| 8,293,265 B2 | 10/2012 | Paulsen |
| 8,496,969 B2 | 7/2013 | Wynn |
| 8,512,787 B2 | 8/2013 | Paulsen |
| 8,758,814 B2 | 6/2014 | Shah |
| 8,807,979 B2 | 8/2014 | Sowden |
| 8,865,240 B2 | 10/2014 | Paulsen |
| 9,107,807 B2 | 8/2015 | Sowden |
| 2001/0043947 A1 | 11/2001 | Robinson |
| 2002/0122822 A1 | 9/2002 | Bunick |
| 2003/0049316 A1 | 3/2003 | Robinson |
| 2003/0175336 A1 | 9/2003 | Luber |
| 2003/0175339 A1 | 9/2003 | Bunick |
| 2004/0109889 A1 | 6/2004 | Bunick |
| 2004/0241208 A1 | 12/2004 | Sowden |
| 2004/0265372 A1 | 12/2004 | Wynn |
| 2004/0265373 A1 | 12/2004 | Wynn |
| 2005/0158383 A1 | 7/2005 | Boehm |
| 2006/0039967 A1 | 2/2006 | Ohta |
| 2006/0121092 A1 | 6/2006 | Ream |
| 2006/0121093 A1 | 6/2006 | Ream |
| 2006/0141009 A1 | 6/2006 | Huron |
| 2007/0128251 A1 | 6/2007 | Paulsen |
| 2008/0075759 A1 | 3/2008 | Paulsen |
| 2009/0214445 A1 | 8/2009 | Boghani |
| 2009/0258039 A1 | 10/2009 | Bunick |
| 2009/0280159 A1 | 11/2009 | Paulsen |
| 2010/0010101 A1 * | 1/2010 | Cherukuri ........... A61K 9/1694 514/770 |
| 2010/0087492 A1 | 4/2010 | Uohnson |
| 2010/0092555 A1 | 4/2010 | Wynn |
| 2010/0312652 A1 | 12/2010 | Boghani |
| 2011/0223234 A1 | 9/2011 | Paulsen |
| 2012/0009129 A1 | 1/2012 | Brzeczko |
| 2012/0039957 A1 | 2/2012 | Brzeczko |
| 2012/0141574 A1 | 6/2012 | Paulsen |
| 2013/0071476 A1 | 3/2013 | Cherukuri |
| 2013/0252979 A1 | 9/2013 | Meier |
| 2013/0330408 A1 | 12/2013 | Uacobs |
| 2013/0331348 A1 | 12/2013 | Paulsen |
| 2014/0141055 A1 * | 5/2014 | Kluger ............... A61P 43/00 424/441 |
| 2015/0224052 A1 | 8/2015 | Paulsen |
| 2015/0307504 A1 | 10/2015 | Singh |

FOREIGN PATENT DOCUMENTS

| | | |
|---|---|---|
| WO | 1996/018387 A1 | 6/1996 |
| WO | 1997/039747 A1 | 10/1997 |
| WO | 03/026613 A1 | 4/2003 |
| WO | 2004/014143 A1 | 2/2004 |
| WO | 2006/036552 A2 | 4/2006 |
| WO | 2006/127494 A2 | 11/2006 |
| WO | 2006/127498 A2 | 11/2006 |
| WO | 2006/127559 A2 | 11/2006 |
| WO | 2006/127616 A9 | 11/2006 |
| WO | 2006/127618 A9 | 11/2006 |
| WO | 2006/127679 A9 | 11/2006 |
| WO | 2006/127680 A9 | 11/2006 |
| WO | 2006/127681 A2 | 11/2006 |
| WO | 2006/127684 A2 | 11/2006 |
| WO | 2006/127685 A2 | 11/2006 |
| WO | 2006/127686 A2 | 11/2006 |
| WO | 2006/127689 A2 | 11/2006 |
| WO | 2006/127690 A2 | 11/2006 |
| WO | 2006/127738 A9 | 11/2006 |
| WO | 2006/127740 A2 | 11/2006 |
| WO | 2006/127741 A9 | 11/2006 |
| WO | 2006/127742 A9 | 11/2006 |
| WO | 2007/052121 A2 | 5/2007 |
| WO | 2007/055696 A1 | 5/2007 |
| WO | 2007/058644 A1 | 5/2007 |
| WO | 2007/058645 A1 | 5/2007 |
| WO | 2007/067582 A2 | 6/2007 |
| WO | 2008/005318 A2 | 10/2008 |
| WO | 2009/064859 A1 | 5/2009 |
| WO | 2010/039892 A1 | 4/2010 |
| WO | 2010/122358 A2 | 10/2010 |
| WO | 2011/079074 A1 | 6/2011 |
| WO | 2011/079248 A1 | 6/2011 |
| WO | 2012/021819 A1 | 2/2012 |
| WO | 2012/090194 A2 | 5/2012 |
| WO | 2013/004250 A1 | 1/2013 |
| WO | 2013/068371 A1 | 5/2013 |
| WO | 2014/079825 A1 | 5/2014 |

OTHER PUBLICATIONS

European Search Report from Application No. EP20160876888 entitled Soft Chew Tablet Pharmaceutical Formulations (dated Jul. 10, 2019).

* cited by examiner

SOFT CHEW PHARMACEUTICAL FORMULATIONS

RELATED APPLICATIONS

The present application is a continuation of U.S. patent application Ser. No. 16/140,477 filed Sep. 24, 2018, entitled SOFT CHEW PHARMACEUTICAL FORMULATIONS, which is a continuation-in-part of U.S. patent application Ser. No. 15/629,354 filed Jun. 21, 2017, entitled SOFT CHEW PHARMACEUTICAL FORMULATIONS, which is a continuation-in-part of International Patent Application No. PCT/US2016/067443 filed Dec. 19, 2016, entitled SOFT-CHEW TABLET PHARMACEUTICAL FORMULATIONS, which claims the benefit of U.S. Provisional Patent Application Ser. No. 62/269,951, filed Dec. 19, 2015, entitled SOFT CHEW TABLETS, each of which is hereby incorporated in its entirety by reference herein.

BACKGROUND

1. Field

The present invention relates to products and processes for the manufacture of soft-chewable tablet pharmaceutical or nutritional dosage forms, for the oral administration of active pharmaceutical ingredients or nutritional agents.

2. Discussion of Prior Art

Chewable pharmaceutical dosage units, such as chewable tablets and soft-chewable tablets, are known and have been commercialized for use with pediatric, geriatric, and involuntary patient populations. Such dosage forms have also been used for subjects that, by instinct, will not accept the medication meant to be swallowed (e.g., animals). Chewable tablets are also useful with competent patients as an alternative to tablets or capsules that must be swallowed whole. The formulation of a drug into a chewable dosage form can increase patient acceptance of a medication in patients that resist or are unable to swallow conventional tablets or capsules.

Conventional dosage forms, such as chewable compressed tablets, using conventional ingredients, can make the tablet gritty or otherwise unappealing to many patients.

Traditionally, tablets compressed on a compression machine are formulated and processed so the tablets have hardness of more than ten kiloponds (10 kp). Tablets having lower hardness levels are discouraged in the prior art to keep the tablet friability acceptable.

A process for manufacturing soft-chewable dosage form for drug delivery is described in U.S. Pat. No. 6,387,381. It discloses a soft-chewable medication vehicle for drug delivery of an active ingredient to animal or human subjects, not containing ingredients of animal origin, without use of heat and without addition of water. The formed mixture was formed into individual chunks using a Formax F6™ molding machine with dies for production of chunk-like shapes, and packaged for storage.

Machines for the production of molded food patties have been described to be useful for the manufacturing of soft-chews for administration to non-human animals. Such machines are molding machines that have been originally developed for use in producing molded food products, for example the Formax F6™ molding machine made by the Formax Corporation.

The use of extruders, forming machines and rotary molding machines exhibit problems associated with the weight and physical forms of a final dosage form. Moreover, the use of such technologies may require conditioning of the final dosage form (e.g. drying or curing final formed structure) for consolidation of shape and structure of formed dosage form. Further, the use of such technologies, equipment and processes is complex, cumbersome, and not traditionally employed by typical pharmaceutical manufacturing facilities producing solid oral dosage forms.

Thus, there is a need for processes of manufacturing soft-chew tablet formulations on a large scale using commonly installed pharmaceutical manufacturing equipment such as a rotary (tablet) compression press.

SUMMARY OF THE INVENTION

The following brief summary is provided to indicate the nature of the subject matter disclosed herein. While certain aspects of the present invention are described below, the summary is not intended to limit the scope of the present invention.

The present invention overcomes the disadvantages and shortcomings of known chewable dosage forms by providing a simplified manufacturing process for soft-chewable dosage unit formulation comprising a highly palatable composition to patients, which is formed by conventional compression techniques using conventional pharmaceutical equipment, such as a rotary tablet press.

It has been found that many conventional soft-chew tablet formulations, made in the prior art using molding or extrusion techniques, can be manufactured more efficiently, reliably, and reproducibly, using a tablet press. The compressed soft-chew dosage forms of the current invention have hardness of less than 2 kp, or may have hardness of less than 1 kp, or may have no measurable hardness when tested with a conventional tablet hardness tester. Despite the low hardness, such compressed soft tablets have friability of less than 1.0%, or less than 0.5%, or less than 0.1% for 100 rotations (according to United States Pharmacopeia (USP) test <1216>); 200 rotations or 300 rotations.

Dosage forms of the present invention include palatable, soft-chewable pharmaceutical compositions for oral administration to an involuntary subject population (e.g., very young children, senile patients, animals, etc.) that includes a therapeutically effective amount of a pharmaceutically active ingredient susceptible to abuse, in an immediate or controlled release form, and a palatability improving agent in an amount sufficient make the pharmaceutical composition palatable to the subject population. As used herein, the phrase "involuntary subject population" is defined as patients who cannot be conventionally instructed to chew and/or swallow conventional hard chew tablets or capsules.

The texture of a chewable dosage unit form is an important factor in the acceptance of oral dosage forms by patients in need of medication. Soft-chewable tablet dosage units, having a soft texture, pleasant mouthfeel, and palatable taste with adequate flavoring agents, provide a solution to such problems. In addition, these features can address the problem of the disagreeable taste of many active pharmaceutical ingredients. Appropriate chewable dosage form can also address texture problems caused by dry dusty, granular, and pulverant properties of many pharmaceutical ingredients.

The soft-chewable formulations are prepared according to methods conventional in the art, such as wet or dry granulation processes.

A soft-chewable pharmaceutical dosage unit is a solid pharmaceutical dosage unit at room temperature that has low hardness and higher moisture content than a conventional tablet or hard chewable tablet. Such a dosage unit exhibits a plastic rheological behavior and can be formed by many manufacturing processes described in prior art into many different shapes. A soft-chewable pharmaceutical dosage unit after forming should be dimensionally stable. The ingredients of such a soft-chewable pharmaceutical dosage unit may be of pharmaceutical grade.

A semi plastic oral dosage form unit has a soft texture and hardness such that the unit is intended to be chewed and swallowed. The texture of the unit is such that it does not appreciably dissolve in the mouth.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Figure 2:
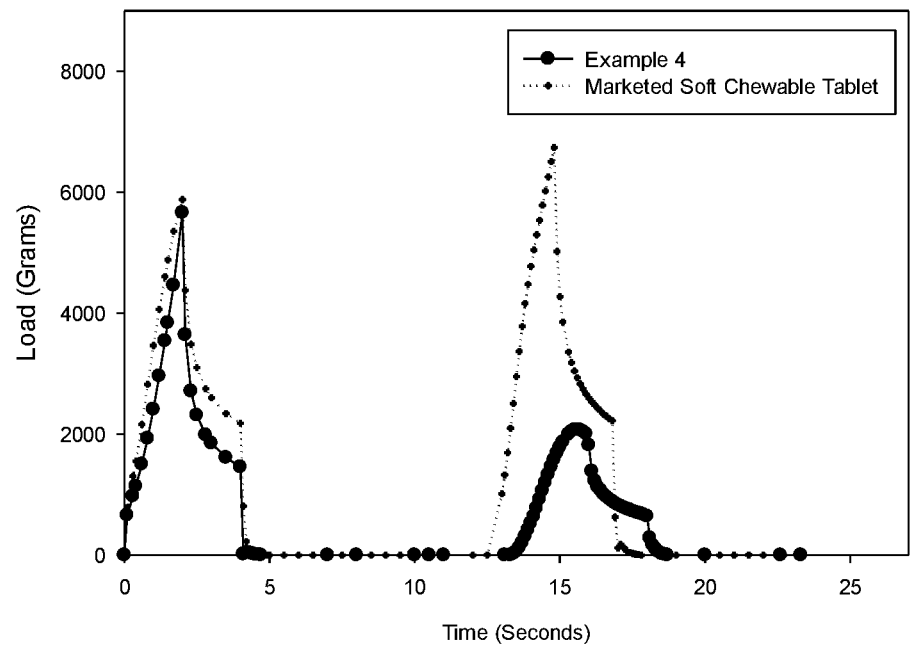
Figure 3:
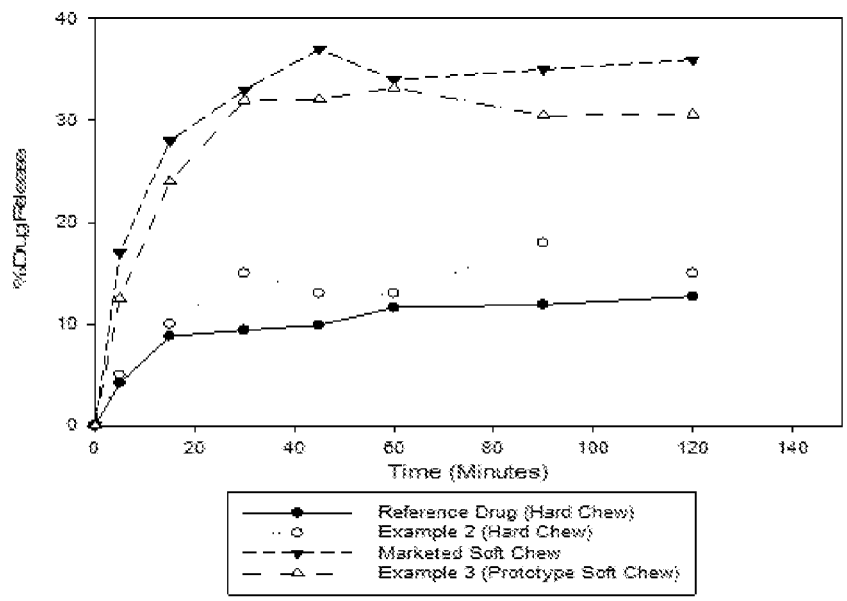
Figure 4:
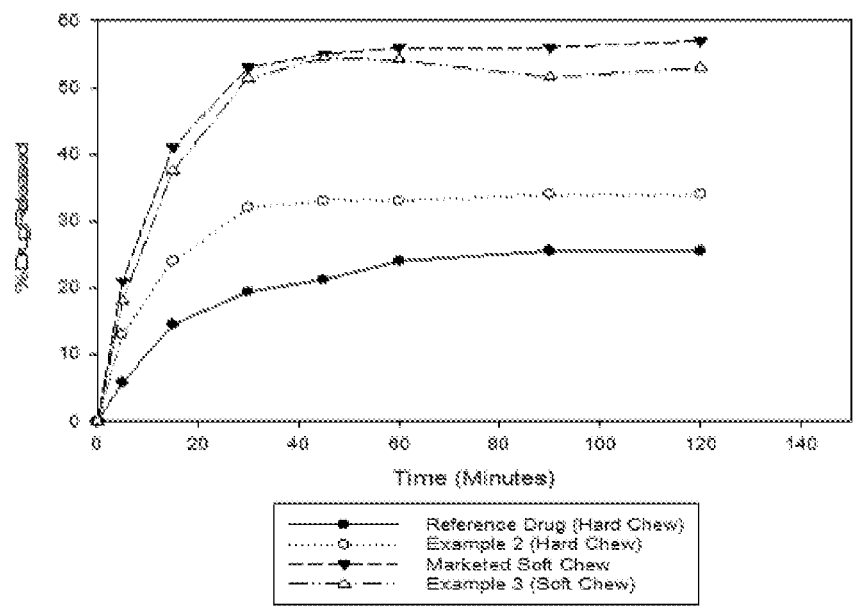
Figure 5:
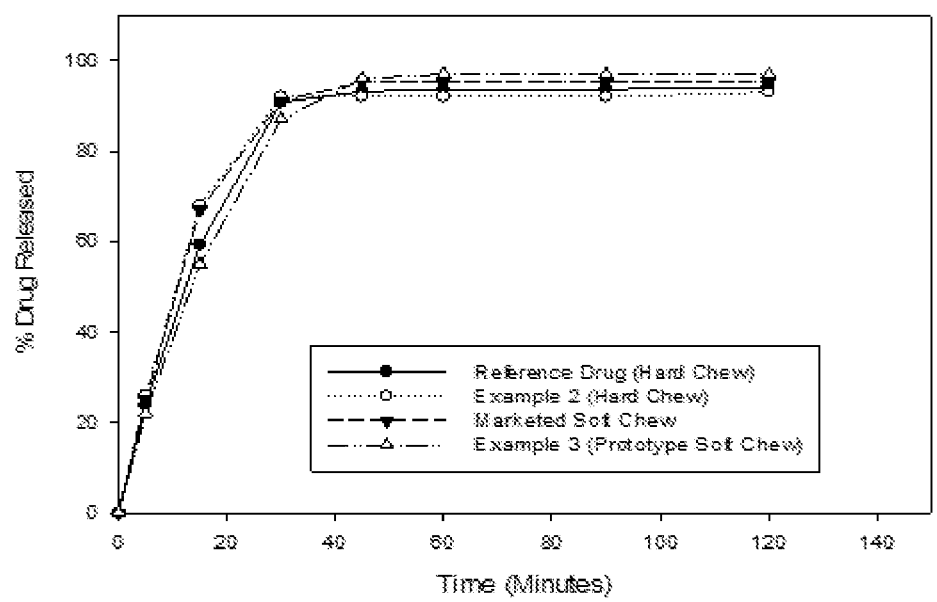
Figure 6:
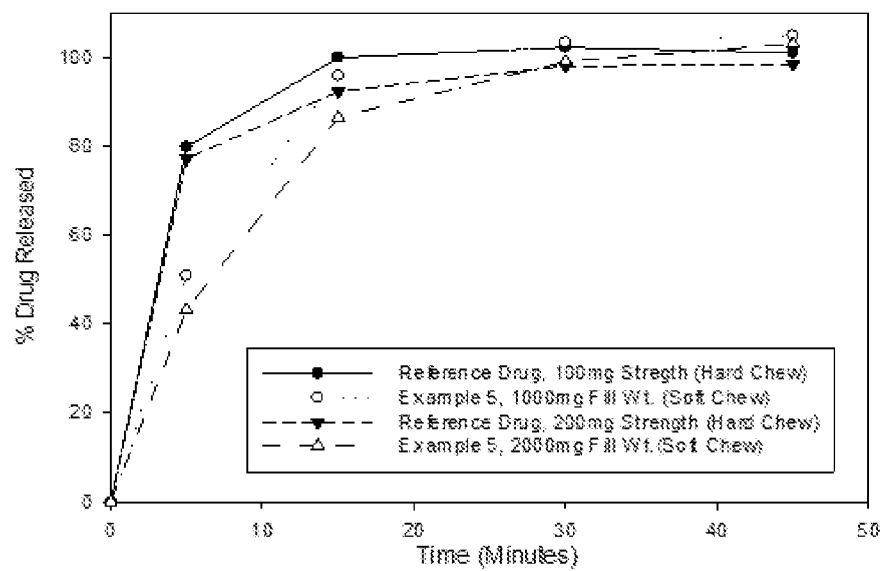
Figure 7:
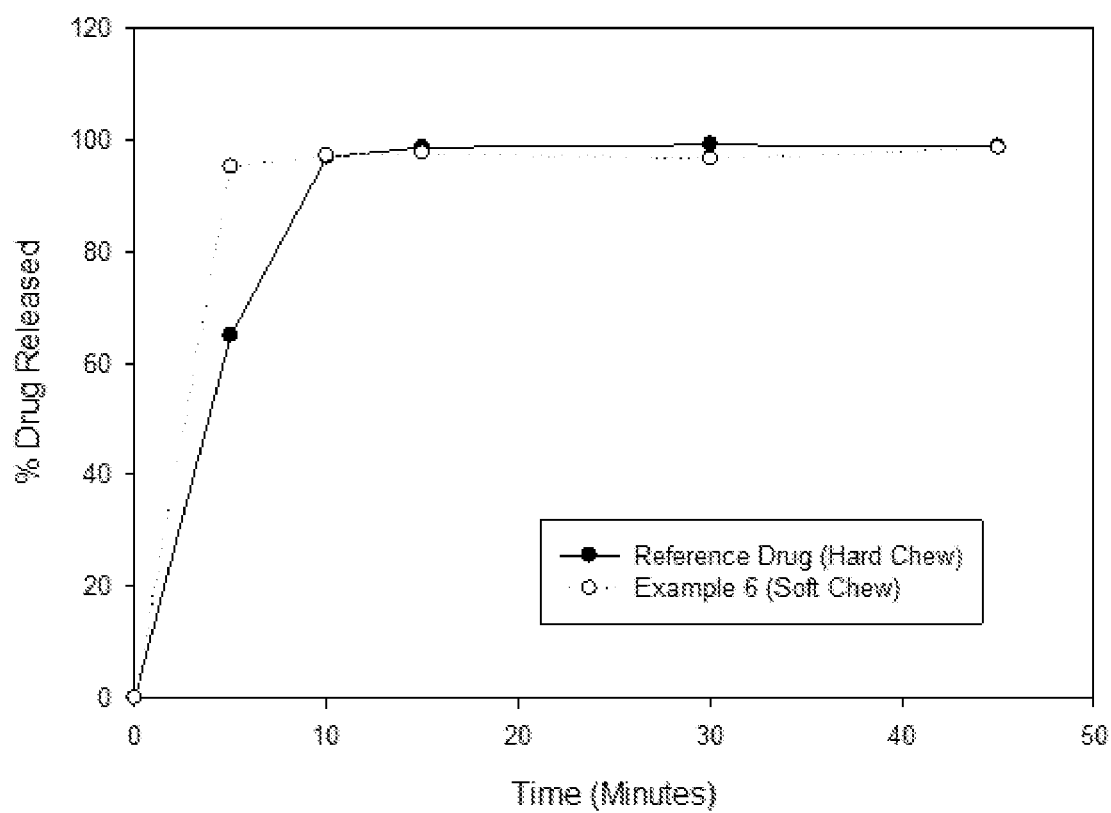

A preferred embodiment of the present invention is described in detail below with reference to the attached drawing figures, wherein:

FIG. 1. is a plot of the texture characterization and comparison to marketed soft-chewable tablet for data in Example 1, showing load peaks applied at 2, 9, and 10 seconds;

FIG. 2. is a plot of the texture characterization and comparison to marketed soft-chewable tablet for data in Example 4, showing load peaks applied at 2, and 15 seconds;

FIG. 3. is a plot of the dissolution vs. time in 0.1 N HCl, USP II apparatus, 900 ml, 100 rpm for data in Tables 7 and 8;

FIG. 4. is a plot of the percent drug release vs. time in acetate buffer, USP II, 900 ml, 100 rpm for data in Tables 9 and 10;

FIG. 5. is a plot of the percent drug release vs. time in phosphate buffer, pH 7.5, USP II apparatus, 900 ml, 100 rpm for data in Tables 11 and 12;

FIG. 6. is a plot of the comparative dissolution of data in Tables 14 and 15, glycine buffer pH 3.0, USP II apparatus, 900 ml, 75 rpm; and FIG. 7. is a plot of the percent drug release v/s time in citrate buffer pH 4.0, USP II apparatus, 900 ml, 100 rpm for data in Table 16.

The drawing figures do not limit the present invention to the specific embodiments disclosed and described herein, with emphasis instead being placed upon clearly illustrating the principles of the preferred embodiment.

DETAILED DESCRIPTION OF THE PREFERRED EMBODIMENTS

The present invention is susceptible of embodiment in many different forms. While the figures show, and the specification describes, certain preferred embodiments of the invention, it is to be understood that such disclosure is by way of example only. There is no intent to limit the principles of the present invention to the particular disclosed embodiments.

The inventors have discovered that by formulation of a soft chew mass according to the present invention, conventional tablet compression techniques (such as a tablet press) can be used to form very soft tablets. Preferably, tablets of the present invention will have a uniform composition.

In certain embodiments of the present invention, dosage forms are formed by making a soft chew mass. The soft chew mass includes various excipients including lipid and dry ingredients, granulation ingredients (granulation aid ingredients and intra-granulation ingredients), extra-granulation ingredients, and active ingredients. During the granulation process, granules of the soft chew mass are formed, passed through appropriate screens for sizing, and then compressed using a rotary tablet press.

The solid, soft chewable or semi-plastic oral dosage forms of the present invention have a soft texture, low hardness, and may be chewed and swallowed. The texture of the unit is such that it does not appreciably dissolve in the mouth. Dosage forms of the present invention may be designed to be chewed and swallowed by a human or an animal.

A tablet press is a mechanical device that compresses powder into tablets of uniform size and weight. A press can be used to manufacture tablets/pellets of a wide variety of materials, including pharmaceuticals, cleaning products, and cosmetics. There are two types of press machines, eccentric-type and rotary-type. The rotary-type is generally more widely used, because it facilitates high production performance with narrow weight variation along with ease of use.

As used herein, the term "fluid" refers a material that is flowable or malleable. A fluid material may be a viscous liquid, with a viscosity comparable, for example, to water, vegetable oil, honey, or peanut butter.

One aspect of the present invention relates to a solid, soft chewable or semi-plastic oral dosage form system including at least one active ingredient. Preferably, the solid, soft chewable or semi-plastic oral dosage forms of the present invention are obtained by compression on a rotary tablet press. Preferably, the solid, soft chewable or semi-plastic oral dosage forms of the present invention exhibit a hardness of less than two kiloponds (2 kp) when measured on tablet hardness tester. More preferably, the solid, soft chewable or semi-plastic oral dosage forms of the present invention exhibit a hardness of less than one kilopond (1 kp) when measured on tablet hardness tester. Even more preferably, the solid, soft chewable or semi-plastic oral dosage forms of the present invention exhibit no hardness when measured on tablet hardness tester. Preferably, the solid, soft chewable or semi-plastic oral dosage forms of the present invention have a friability of less than about 1% at 100 rotations.

In one embodiment of the present invention, a soft-chew mass is formed by blending appropriate active ingredients and excipients. The soft-chew mass is compressed in tablet press to provide tablets with minimal hardness. Preferably, the tablets of the present invention have a hardness less than or equal to about two kiloponds (2 kp). More preferably, the tablets of the present invention have a hardness of less than or equal to about one kilopond (1 kp). Even more preferably, the tablets of the present invention have no measurable hardness in a tablet hardness testing apparatus.

In one embodiment of the present invention, a process is provided for the manufacture of a compressed soft-chew tablet unit dosage form for the oral administration of an active ingredient, in which a soft-chew tablet or semi-plastic tablet is formed by compressing a soft-chew mass on a compression press, and wherein the soft-chew tablets have a hardness of less than about two kiloponds (2 kp) and a friability of less than about one percent (1%) at three-hundred (300) rotations.

In certain embodiments of the present invention, a process is provided for the manufacture of a compressed soft-chew tablet unit dosage form for the oral administration of an active ingredient, in which a soft-chew mass mixture is provided including an active ingredient, wherein the soft-chew mass is a granulate (granules) formed with a granulation and sifting step, and wherein the soft-chew mass granulate is pressed into tablets using a tablet press, and wherein the soft-chew tablets have a hardness of less than about two kiloponds (2 kp) and a friability of less than about one percent (1%) at three-hundred (300) rotations.

In certain embodiments of the present invention, an edible compressed soft-chew tablet or semi plastic oral unit dosage form is manufactured by a process of: (a) mixing at least one active ingredient with at least one dry or liquid component to form a liquid premix; (b) blending dry ingredients having at least one of each of a bulking agent, a lipid, a flavoring agent, a disintegrating agent, a binding agent, a surfactant, a preservative, a lubricating agent, and an anti-sticking to form a uniform dry ingredient mixture; (c) blending the premix and the uniform dry ingredient mixture to form a granulated compacted soft-chew mass; (d) sifting the granulated compacted soft-chew mass through at least one sifting screen to form uniform granules of the soft-chew mass; and (e) adding a lubricant or anti sticking agent to the uniform granules of the soft-chew mass and compressing the resulting mixture in a tablet press to from soft-chew tablets.

In certain embodiments, two or more mixtures are prepared in the inventive process. A first mixture is a fluid premix containing the active ingredient, and a second mixture is a blend of dry ingredients. The fluid premix and dry ingredient blend may be blended together to form a soft-chew mass.

As used herein, the term "active ingredient" or "active agent" refers to an active pharmaceutical ingredient or nutritional agent.

An active pharmaceutical ingredient is a substance used in a pharmaceutical dosage form, intended to furnish pharmacological activity or to otherwise have direct effect in the diagnosis, cure, mitigation, treatment or prevention of disease, or to have direct effect in restoring, correcting or modifying physiological functions in a patient population (humans or animals).

A nutritional agent may include vitamins, minerals, glycosaminoglycan or its active members, amino acids or combination thereof that are useful in human or animal nutrition.

An active pharmaceutical ingredient may include any approved or experimental drug. By "approved," it is meant that the drug is approved for human or veterinary use by a regulatory agency in any country that makes such drug approvals. For example, the pharmaceutically active ingredient may be selected from an anesthetic agent, anthelmintic agent, analgesic agent, steroid, corticosteroid agent, non-steroidal anti-inflammatory drug (NSAID) agent, antiemetic agent, anti-thyroidal agent, parasiticidal agent, appetite stimulant, antihistamine agent, antifungal agent, antiprotozoal agent, or anti-depressant.

In certain embodiments of the present invention, the active ingredient may be in granular form and coated, or further coated, with a suitable coating. For example, the coating could be a coating polymer that coats and protects the active ingredient, or masks an offensive taste and/or offensive odor. In certain embodiments, the coating could be a functional coating (e.g., an extended-release coating, delayed-release coating, controlled-release coating, barrier coating, or a combination thereof).

In certain embodiments of the present invention, the active ingredient may be dissolved, emulsified, or suspended in a non-aqueous solvent before addition. The nutritional or pharmaceutically active ingredient may be soluble, partially soluble, or insoluble in water.

In certain embodiments of the present invention, the active ingredient is added to the composition by dry blending.

In certain embodiments of the present invention, the active ingredient may be conjugated with other ingredients, such as cyclodextrins, surfactants, solubility or bioavailability enhancers, etc., to inhibit interactions with other excipients or with the environment, or to promote the chemical stability, improve solubility, enhance bioavailability, or improve the palatability of the nutritional ingredient or pharmaceutically active agent. Similarly, the pharmaceutically active ingredient may be incorporated into a novel drug delivery system, such as microspheres, microcapsules, liposomes, niosomes, nanoparticles, microemulsions, or nanoemulsions to protect the drug or permit organ targeting.

In certain embodiments of the present invention, the rate of release of the active ingredient may be modulated or controlled by, for example, the use of controlled or sustained release agents (e.g., polymers) or by using excipients (e.g., disintegrants) that promote in rapid release, as appropriate.

In certain embodiments of the present invention, a single excipient has more than one function in the formulation of the present invention. For example, propylene glycol and glycerol may be present and have a simultaneous role as a plasticizer, humectants, antimicrobial agents, or any combination of any two or more thereof, in this formulation. Lipids may have a role as a lubricant, plasticizer, binders, or any combination of any two or more thereof. Any suitable excipient may be used. Lipids may include, but are not limited to, mineral oils, liquid vegetable oils, or solid hydrogenated vegetable oils. Vegetable oils may include, but are not limited to, soybean oil, olive oil, flaxseed oil, canola oil, or corn oil.

In certain embodiments of the present invention, the active ingredient may be mixed with a lipid (e.g., vegetable oil) to form a premix.

In certain embodiments, the composition of the solid, soft chewable or semi-plastic oral dosage form of the present invention includes a texturing agent, selected from the group comprising of modified corn starches, polyols, poly(ethylene) oxide, microcrystalline cellulose co-processed with guar gum and the like. A polyol may include propylene glycol, glycerin, polyethylene glycol and mixtures thereof.

In certain embodiments, the composition of the solid, soft chewable or semi-plastic oral dosage form of the present invention includes one or more fillers. A filler may be used to increase the total mass of the chewable formulation to a manageable size or to enhance the flow properties of final powder or granules to be compressed in a rotary tablet press.

In certain embodiments, the composition of the solid, soft chewable or semi-plastic oral dosage form of the present invention includes a binding agent. The binding agent may be polyethylene glycol. The polyethylene glycol may be admixed to dry ingredients for mixing. The polyethylene glycol may be melted and added to at least one other dry ingredient and mixed to form the uniform dry ingredient mixture.

In certain embodiments, the composition of the solid, soft chewable or semi-plastic oral dosage form of the present invention includes microcrystalline cellulose as a bulking agent.

In certain embodiments, the composition of the solid, soft chewable or semi-plastic oral dosage form of the present invention includes lipid and microcrystalline cellulose in a ratio of about 2:1 to about 1:2.5, w/w, and wherein the tablet is manufactured by compression on a tablet press.

In certain embodiments of the present invention, one or more diluents may be used in combination with silicified microcrystalline cellulose. Examples of diluents include starches and their derivatives (e.g., hydrogenated starch hydrolysate), celluloses and their derivatives (e.g., cellulose acetate), protein matrices (soy protein, dextrates, wheat gluten, whey, corn cob, corn gluten), carbohydrates (e.g., maltodextrin, polydextrose), sugars and sugar alcohols (glucose, lactose, fructose, maltose, dextrose, sucrose, maltitol, xylitol, isomalt, mannitol), silicates, calcium phosphates, calcium sulfate, dextrates, kaolin, magnesium carbonate, polymethacrylates, talc, salts (e.g., sodium chloride) or any combination of any two or more thereof.

In certain embodiments, the composition of the solid, soft chewable or semi-plastic oral dosage form of the present invention includes a starch, or a modified starch, or a mixture of starch and a modified starch.

In certain embodiments of the present invention, diluents may also serve a role in fat or oil absorption, disintegration, and binding, providing nutrition, lubrication or any combination of any two or more thereof. The diluents may also be used for taste masking or modifying texture, for example microcrystalline cellulose co-processed with guar gum and/or modified corn starches.

In certain embodiments, the composition of the solid, soft chewable or semi-plastic oral dosage form of the present invention includes one or more binders. Binders improve the binding properties of the compacted mass, to assist the formation of compact dosage units. Any suitable binder known in the art may be used. For example, binders that may be used according to the present invention may include, but are not limited to gums (e.g., xanthan gum and guar gum), alginates, celluloses and their derivatives (e.g., methylcellulose and microcrystalline cellulose), lipids (e.g., fats and oils), starches and their derivatives, dextrins, povidones, silicates, polymethacrylates, polyethylene oxides, waxes, chitosan, polycarbophil, agar, carbomers, and combinations of the foregoing.

In certain embodiments, the composition of the solid, soft chewable or semi-plastic oral dosage form of the present invention includes one or more palatability enhancers. Palatability enhancers improve the taste of material that is chewed. Advantageously, palatability enhancers may improve the palatability of soft-chewable formulations comprising bitter, acrid, obnoxious, unpleasant, or otherwise unpalatable nutritional or pharmaceutically active agents.

In certain embodiments of the present invention, the palatability enhancer is a taste masking agent, a flavoring agent, an aroma modifier, or a taste modifier, or any combination of any two or more thereof.

Flavoring agents may be used to improve the palatability of the chewable tablets. Any type of flavoring agent can be used provided it improves the palatability of the product, typically by improving either its taste and/or smell. The use of a flavoring agent may also assist with dose compliance. Flavors can be natural (derived from animal or plant sources), semisynthetic, or artificial. In one embodiment, the flavoring agent is an artificial flavoring agent, semi-synthetic flavoring agent, a natural flavoring agent, or nature identical flavoring agent.

In certain embodiments, the composition of the solid, soft chewable or semi-plastic oral dosage form of the present invention includes liquid components that are absorbed on the surface of a lipid absorbing pharmaceutical ingredient selected from one or more of microcrystalline cellulose, silicified microcrystalline cellulose, and a combination of microcrystalline cellulose and guar gum. The liquid components absorbed on the surface of the lipid absorbing pharmaceutical ingredient may be mixed with the dry ingredient mixture and then sifted again through at least one sifting screen to form further granules of the soft-chew composition mixture. In an embodiment, a nutritional agent or a pharmaceutically active ingredient is admixed with the liquid components prior to mixing with the lipid absorbing pharmaceutical ingredient.

In certain embodiments of the present invention, plasticizers may be used to the formulation to improve plasticity and malleability of dosage units of the present invention. In one embodiment, a plasticizer may be selected from alcohols, glycols (such as propylene glycol), lanolin, wool fat, liquid paraffin, mineral oil, petrolatum, benzyl phenylformate, chlorobutanol, diethyl phthalate, glycerol, polyethylene glycol, propylene glycol, sorbitol, triacetin, benzyl phenyl formate, dibutyl sebacate, tributyl citrate, triethyl citrate, or any combination of any two or more thereof. Other plasticizers known in the art may also be used.

In certain embodiments, the composition of the solid, soft chewable or semi-plastic oral dosage form of the present invention includes a non-active ingredient including of one or more of a starch, a polysaccharide, a humectant, a polyol, water-soluble poly(ethylene oxide) resin.

In certain embodiments, the composition of the solid, soft chewable or semi-plastic oral dosage form of the present invention includes a humectant. A humectant is used to retain moisture in the dosage unit. A humectant of value in this invention may be selected from sodium and potassium chloride, benzalkonium chloride, aluminum silicate, sodium propionates, sodium and potassium phosphates, sugars, sulfites, hydrogenated starch hydrolysate, etc. Liquid humectants include, but are not limited to, glycols, polyols, sugar alcohols, vegetable oils and mineral oil, hydrogenated vegetable oils, hydrocarbons, triacetin, liquid paraffin, or any combination of any two or more thereof. Other humectants known in the art may also be used.

In certain embodiments, the composition of the solid, soft chewable or semi-plastic oral dosage form of the present invention includes an antioxidant. An antioxidant inhibits oxidation and may be of benefit as a preservative, or to maintain the chemical stability of an active or inactive ingredient. An antioxidant may be selected from propyl gallate, ascorbic acid and its derivatives, sodium formaldehyde sulfoxylate, malic acid, fumaric acid, editic acid, thiols, polyphenols, sodium ethylenediaminetetraacetic acid ("EDTA"), sodium ascorbate, sodium metabisulfite, butylated hydroxytoluene, butylated hydroxyanisole, butylated hydroxyanisole and butylated hydroxytoluene co-processed with *Zea mays* oil or natural substances such as flavonoids, tocopherols, carotenes, cysteine, or any combination of any two or more thereof. Other antioxidants known in the art may also be used. The antioxidants are generally added to the formulation in amounts of from about one one-hundredth percent (0.01%) to about two percent (2.0%), based upon total weight of the formulation, with about one one-hundredth percent (0.01%) to about one percent (1.0%) being especially preferred.

In certain embodiments, the composition of the solid, soft chewable or semi-plastic oral dosage form of the present invention includes a preservative selected from the group including parabens (methylparaben and/or propylparaben), benzalkonium chloride, benzethonium chloride, benzoic acid, citric acid, fumaric acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, potassium sorbate, sodium benzoate, sodium propionate, sorbic acid, thimerosal, and quaternary ammonium compounds. Other preservatives known in the art may also be used.

In certain embodiments, the composition of the solid, soft chewable or semi-plastic oral dosage form of the present invention includes a nonaqueous solvent, for example glycerin or sorbitol. A non-aqueous solvent may disperse, solubilize or enhance solubilization of the nutritional or pharmaceutically active agent. The non-aqueous solvent may also enhance the binding of the formulation and the consistency and texture of the soft-chewable dosage form.

In certain embodiments, the composition of the solid, soft chewable or semi-plastic oral dosage form of the present invention includes a disintegrating agent. A disintegrating agent may be used to enable the inventive chewable tablets to break down on contact with water, saliva, or gastric fluid in the stomach to quickly release the active ingredient. A disintegrating agent may be selected from povidones, croscarmellose sodium, sodium starch glycollate, celluloses and their derivatives, starches and their derivatives, gelatin, silicon dioxide, or any combination of any two or more thereof. Other disintegrating agents known in the art may also be used. Disintegration may be tested and measured using United States Pharmacopeia (USP) Disintegration Test <701> for uncoated tablets, using water as medium.

In certain embodiments of the present invention, a granulated compacted soft-chew mass is formed, and the mass is dried by equipment using direct or indirect conduction heat applied to a static solid bed, a moving solid bed, or a fluidized solid bed. The granulated mass may be dried at room temperature, for example about twenty-five degrees Celsius (25° C.) plus-or-minus ten degrees Celsius (10° C.). Alternatively, the granulated mass may be dried at a controlled temperature of about fifty degrees Celsius (50° C.) or less.

In certain embodiments of the present invention, the process of this invention may include sifting, or milling, of dry components or a granulated mass, or a mixture of both through sifting screens with mesh sizes commonly known in the art. Mesh sizes for sifting screens may include Mesh #4 or 5 or 6 or 7 or 8 or 10 or 12 or 14 or 16 or 18 or 20 or 25 or 30 or 35 or 40 or 45 or 50 or 60 or other mesh sizes commonly known in the art. Components may be sifted through at two or more screens with different mesh sizes one after other in gradual or random order of mesh sizes.

In certain embodiments of the present invention, the dry ingredient mixture or the granulated compacted soft-chew mass is sifted through sifting equipment using impaction, attrition, compression or cutting.

In certain embodiments of the present invention, the dry ingredient mixture or the granulated compacted soft-chew mass is uniformly mixed using equipment using diffusion mixing, convection mixing or pneumatic mixing.

In certain embodiments of the present invention, the process of this invention may employ pre-compression force applied to the granulated compacted soft-chew mass before application of main compression force for compression of soft-chews.

In certain embodiments of the present invention, the granulated compacted soft-chew mass is fed into a compression die by gravity feed, power assisted feed, by centrifugal force, or by compression coating.

In certain embodiments of the present invention, the soft-chew tablets of this invention may incorporate an abuse-deterrent technology, which can include one or more of high-melting-point excipients that resist heating and injecting; taste modifiers that resist covert administration, snorting (ingestion of a powdered material through the nose) and dose dumping (extraction of active pharmaceutical ingredients (API) from tablets); water insoluble excipients that resist extraction and drink adulteration; waxy excipients that resist snorting; viscosity modifiers that resist dissolution, injection and dose dumping; low-density excipients that resist drink adulteration; and dyes, that resist adulteration.

The breaking force of tablets is commonly called hardness in the pharmaceutical literature. The term crushing strength is also frequently used to describe the resistance of tablets to the application of a compressive load.

The measure of the mechanical integrity of tablets is their breaking force or hardness, which is the force required to cause them to fail (i.e., break) in a specific plane. Various equipment is used for hardness measurements, for example a Monsanto Hardness Tester, Stokes Hardness tester, Pfizer Hardness Tester, Strong-Cobb Hardness Tester, or Schleuniger Hardness tester. Tablet hardness can be expressed using various units depending on the equipment used for hardness measurement. The units for tablet hardness measurement are newtons, pounds, Strong-Cobb units, and kiloponds.

For the hardness measurements for exemplarily examples in this invention, a Schleuniger Hardness tester was used, and hardness was measured in kiloponds or newtons. This apparatus has two parallel platens between which a tablet is placed. A load is applied and the value of the hardness is measured. The platen faces are polished smooth and precision-ground perpendicularly to the direction of movement. Perpendicularity is preserved during platen movement, and the mechanism is free of any bending or torsion displacements as the load is applied. The contact faces are larger than the area of contact with the tablet.

In one embodiment, the chewable formulation of this invention includes dosage units which have hardness of less than two kilopond (2 kp), preferably less than one kilopond (1 kp), and more preferably has no measurable hardness when measured with a tablet hardness tester.

In certain embodiments of the present invention, the chewable formulation of this invention includes dosage units with hardness less than three (3.0) Strong Cobb units, preferably less than one and one-half (1.5) Strong Cobb units, or more preferably no measurable hardness when measured with a tablet hardness tester.

In certain embodiments of the present invention, the chewable formulation of this invention includes dosage units with hardness less than five (5.0) pound, preferably less than two and one-half (2.5) pound, or more preferably no measurable hardness when measured with a tablet hardness tester.

In certain embodiments of the present invention, the chewable formulation of this invention includes dosage units with hardness less than twenty (20.0) newtons, preferably less than ten (10) newtons, or more preferably no measurable hardness when measured with a tablet hardness tester.

A friability value of about one percent (1%) or less (when measured as per USP test) is desirable for tablets in order for them to withstand the stress of handling during production, packaging, and transport.

In one embodiment the formulation comprises of dosage units with friability less than one percent (1%), preferably less than one-half percent (0.5%), or more preferably less than one-tenth percent (0.1%) for one-hundred (100) rotations (per USP), or two-hundred (200) rotations, or three-hundred (300) rotations.

For traditional tablet compression using rotary tablet press, tablet hardness is traditionally kept three kilopond (3 kp) or more. As dosage form size increases, compression force is increased to produce tablet with even higher hardness.

For tablets having hardness five kilopond (5 kp) or less, a high order of tablet rejection results because of stress during production, packaging, and transport. For such tablets tablet friability is generally between one-tenth percent (0.1%) and one percent (1.0%) when performed as per USP test.

As tablet hardness decreases, tablet friability generally increases. But the instant inventors have unexpectedly found that for exemplarily formulations herein, soft-chewable tablets with hardness less than two kilopond (2 kp) or lower, friability remains less than one percent (1%), preferably less than one-half percent (0.5%), more preferably less than one-tenth percent (0.1%) for one-hundred (100) rotations (per USP), two-hundred (200) rotations, or three-hundred (300) rotations.

In one embodiment, the soft-chewable tablet maintains a characteristic selected from chewiness, hardness, compression energy, adhesion, cohesiveness, springiness, and modulus, and any combination of any two or more thereof (when measured by the texture analyzer as per procedure for Example 1) sufficient to provide a chewable texture.

In one embodiment, the dosage unit of this invention (e.g., soft-chew) has a weight between about one-tenth gram (0.1 g) and about ten grams (10 g). In one embodiment, the dosage unit has a weight between about one-half gram (0.5 g) and about four grams (4.0 g). In one embodiment, the dosage unit has a weight between about one-tenth gram (0.1 g) and about three grams (3.0 g). In another embodiment, the weight of the dosage unit is between about one-tenth gram (0.1 g) and about two grams (2.0 g).

In certain embodiments of the present invention, weight of the dosage unit can be between about one-tenth gram (0.1 g) and about one gram (1.0 g); or between about one and one-tenth gram (1.1 g) and about two grams (2.0 g); or between about two and one-tenth grams (2.1 g) and about three grams (3.0 g); or between about three and one-tenth grams (3.1 g) and about four grams (4.0 g); or between about four and one-tenth grams (4.1 g) and about five grams (5.0 g).

In certain embodiments of the present invention, the dosage unit (e.g., soft-chew) of this invention can have an imprint on at least one surface of the dosage unit. In a specific embodiment this imprint can be on the top surface of the dosage unit. Such imprint can be, for example, letters, numbers, logos, or symbols, etc. An imprint can also be on the bottom surface.

In one embodiment, the dosage unit has a score or groove on one of the surfaces. This cross score has the effect that it facilitates the dividing of the dosage unit and allows more exact dosing of the active pharmaceutical ingredient according to the body weight, and/or age of the patient.

Such dosage units can have different weights, dimensions and shapes that can be adapted to the weight and need of the target patient population to allow accurate dosing. Dosage forms can be to different weights, dimensions and shapes known in the art. For example, the soft-chew tablets of this invention can be round, capsule-shaped, or have a modified shape.

The soft-chewable tablets of this invention can be packaged as bulk primary packaging, or as singular unit primary packaging.

EXAMPLES

The following Examples set forth preferred therapeutic agents and methods in accordance with the invention, but it is to be understood that these examples are given by way of illustration only, and nothing therein should be taken as a limitation upon the overall scope of the invention.

Ingredients corresponding to Example 1 are tabulated in Table 1, with the amount of each ingredient given in respective percent by weight (% w/w).

TABLE 1

| Ingredients | % w/w |
| --- | --- |
| Active | |
| Placebo Active | 3.00 |
| Granulation Aid Ingredients | |
| Soybean Oil | 15.00 |
| Zea Mays (corn) Oil & butylated hydroxyanisole (BHA) & butylated hydroxy toluene (BHT) | 0.10 |
| Glycerin | 19.00 |
| Intra-granular Ingredients | |
| Microcrystalline Cellulose | 21.00 |
| Pregelatinized Corn Starch | 5.00 |
| Extra-granular Ingredients | |
| Pregelatinized Corn Starch | 3.00 |
| Beef Flavor | 19.00 |
| Sodium Lauryl Sulfate | 0.20 |
| Poly(ethylene) Oxide | 1.00 |
| Maltodextrin | 3.00 |
| Modified Corn Starch | 3.00 |
| Croscarmellose Sodium | 3.70 |
| Color | 0.01 |
| Polyethylene Glycol 3350 | 2.00 |
| Flow Aid Ingredients | |
| Magnesium Stearate | 1.00 |
| Colloidal Silicon Dioxide | 1.00 |
| Total | 100 |

Procedure—Example 1

Step 1: Two methods were employed using the formulation summarized in Table 1. In the first method, a placebo active was added as part of granulation aid components, and in the second method placebo active was added as part of extra-granular addition, remaining procedure was same for both methods.

Step 2: The intra-granular ingredients and the active were passed through a sifting screen followed by uniform mixing.

Step 3: The extra-granular ingredients were passed through a sifting screen followed by uniform mixing.

Step 4: Granulation aid components were added to the intra-granular blend and mixed thoroughly until uniformly mixed, followed by melting polyethylene glycol 3350 and quickly adding this to granulated mass, followed by uniform mixing.

Step 5: The granulated mass from Step 4 was passed through a sifting screen to form uniform granules.

Step 6: The extra-granular blend from Step 3 was added to screened granules from step 5, followed by uniform mixing.

Step 7: Blended granules from Step 6 were passed through a sifting screen.

Step 8: Magnesium stearate and colloidal silicon dioxide mixed with small amount of granules from Step 6 and passed sifting screen.

Step 9: The milled (sifted) components from Step 8 were added to granules from Step 6 followed by uniform mixing followed by compressing on a rotary tablet press using 18 mm×18 mm rounded square punch.

Texture Analysis was performed using CT3 Texture Analyzer (Brookfield Engineering) using a TA3/100 probe and twenty-five-thousand gram (25,000 g) load cell and five gram (5 g) trigger load, over four millimeters (4 mm) using two millimeter per second (2 mm/s) test speed and using a data rate of one-hundred (100) points/second. Load peaks were applied at two (2), nine (9), and ten (10) seconds. The results are plotted in FIG. 1.

The results of a tablet characterization study are tabulated in Tables 2 and 3. In the study, tablets formed in accordance with Example 1 were compared to a marketed soft-chewable tablet. The marketed soft-chewable tablet was formed using an unconventional molding method. The data in Table 3 was obtained using a CT3 Texture Analyzer.

TABLE 2

| Parameters | Marketed Product | Example 1 |
|---|---|---|
| Weight (grams) | 3.600-3.750 | 3000 |
| Shape | Trapezoidal | Square |
| Color | Multiple Strengths with Different Colors | Yellowish Brown |
| Width × Length Top (mm) | 16.10 × 17.40 | 18 × 18 |
| Width × Length Bottom (mm) | 17.80 × 18.60 | 18 × 18 |
| Thickness (mm) | 9.20-9.60 | 8.00-9.00 |
| Disintegration Time (minutes) | 20-26 | 10 to 15 |
| Tablet Hardness (kp) | 0 | 0 |
| Tablet Friability (%) | 0 | 0 |

TABLE 3

| Parameters | Marketed Product | Example 1 |
|---|---|---|
| Hardness (grams) | 3000-3900 | 3698.00-3866.00 |
| Deformation at Hardness (mm) | 3.95-4.00 | 1.78-3.58 |
| Adhesiveness | 0.00 mJ-0.20 mJ | 0.00 mJ-0.10 mJ |
| Cohesiveness | 0.30-0.34 | 0.00-0.15 |
| Gumminess | 1100.00 g-1450.00 g | 4.00 g-546.00 g |
| Chewiness | 24.40 mJ-93.70 mJ | 0.00 mJ-42.70 mJ |

Ingredients corresponding to Example 2 (a conventional hard chewable tablet) are tabulated in Table 4, with the amount of each ingredient given in respective percent by weight (% w/w).

TABLE 4

| Ingredients | % w/w |
|---|---|
| Step 1 Ingredients | |
| Carprofen | 5.00 |
| Artificial Beef Flavor | 20.00 |
| Silicified Microcrystalline Cellulose | 17.95 |
| Polycarbophil | 2.50 |
| Polyethylene Glycol 3350 | 6.00 |
| Microcrystalline Cellulose & Guar Gum | 3.00 |
| Pregelatinized Corn Starch | 24.00 |
| Lactose Monohydrate | 15.00 |
| Croscarmellose Sodium | 2.50 |
| Step 2 Ingredients | |
| Color 1 | 0.03 |
| Color 2 | 0.02 |
| Talc | 2.00 |
| Magnesium Stearate | 2.00 |
| Total | 100 |

Procedure—Example 2

Step 1: All step 1 ingredients were individually weighed and passed through a sifting screen and uniformly mixed.

Step 2: The step 2 ingredients were mixed along with small quantity of pre-mix from Step 1.

Step 3: The ingredients from Step 2 were added to the remaining pre-mixed ingredients from Step 1 and mixed for uniform mixing for 2-3 minutes and further subjected to compression on rotary tablet press for 500 mg fill weight.

Ingredients corresponding to Examples 3 and 4 are tabulated in Table 5, with the amount of each ingredient given in respective percent by weight (% w/w).

TABLE 5

| Ingredients | Example 3 | Example 4 |
|---|---|---|
| Active | | |
| Carprofen | 0.84 | 3.34 |
| Granulation Aid Ingredients | | |
| Soybean Oil | 16.00 | 9.00 |
| Zea Mays Oil & BHA & BHT | 0.10 | 0.10 |
| Glycerin | 20.00 | 13.00 |
| Polyethylene Glycol 600 | — | 9.00 |
| Povidone K30 | 2.00 | 2.00 |
| Intra-granular Ingredients | | |
| Polycarbophil | 0.30 | — |
| Silicified Microcrystalline Cellulose | 16.06 | 18.66 |
| Pregelatinized Corn Starch | 7.00 | 7.00 |
| Calcium Sulfate Dihydrate | 1.30 | 2.50 |
| Artificial Beef Flavor | 8.00 | 15.00 |
| Croscarmellose Sodium | 2.5 | 2.5 |
| Polyethylene Glycol 600 | — | — |
| Polyethylene Glycol 3350 | 2 | |
| Extra-granular Ingredients | | |
| Pregelatinized Corn Starch | 4 | 5 |
| Artificial Beef Flavor | 10 | 3 |
| Sodium Lauryl Sulfate | 0.2 | 0.2 |
| Poly(ethylene) Oxide | 1 | 1 |
| Modified Corn Starch | 3 | — |
| Croscarmellose Sodium | 2.5 | 2.5 |

TABLE 5-continued

| Ingredients | Example 3 | Example 4 |
|---|---|---|
| Calcium Sulfate Dihydrate | 1.7 | 1.7 |
| Lactose Monohydrate | 1.5 | 4.5 |
| Total | 100 | 100 |

Procedure—Example 3

Step 1: The active, soybean oil and *Zea Mays* Oil and BHA and BHT are weighed accurately and uniformly mixed to form a dispersion.

Step 2: Simultaneously, a dispersion was prepared by adding povidone to glycerin and properly mixing.

Step 3: Intra granular dry ingredients were passed through a sifting screen followed by uniform mixing.

Step 4: Dispersions from Step 1 and Step 2 were used as granulation aid, adding them one after another to pre-mixed ingredients from Step 3.

Step 5: The formed doughy mass was passed through a sifting screen to get wet granules.

Step 6: Extra-granular ingredients were passed through a sifting screen followed by uniform mixing.

Step 7: Approximately half the quantity of the extra-granular blend from Step 6 was added to the wet granules formed in Step 5 and uniformly mixed.

Step 8: The formed slightly dry granular mass was further passed through sifting screen to obtain granules.

Step 9: The formed granules are uniformly mixed with remaining quantity of extra granular blend from Step 6 and further subjected to compression on rotary tablet press using 18 mm×18 mm rounded square punch for 3.0 gram target fill weight.

Procedure—Example 4

Step 1: Active, soybean oil and *Zea Mays* Oil and BHA and BHT are weighed accurately and uniformly mixed to form a dispersion.

Step 2: Simultaneously, a dispersion was prepared by adding Povidone and Polyethylene Glycol 600 to Glycerin and properly mixing.

Step 3: The Intra-granular dry ingredients were mixed together and passed through a sifting screen.

Step 4: The extra-granular dry ingredients were mixed together and passed through a sifting screen.

Step 5: The pre-mix from step 3 was added to a Rapid Mixer Granulator (RMG) bowl of appropriate size and mixed for 2 minutes with 60 rpm impeller speed.

Step 6: The Dispersion from step 1 was added slowly in about 1 minute and mixed further for 4 minutes with 60 rpm impeller speed and 150 rpm chopper speed.

Step 7: The dispersion from step 2 was added slowly in about 2 minute with 50 rpm impeller speed and 150 rpm chopper speed.

Step 8: The formed doughy mass was passed through a sifting screen to get wet granules.

Step 9: Approximately half the quantity of the extra-granular blend from step 4 was added to the wet granules formed in step 8 and uniformly blended.

Step 10: The formed slightly dry granular mass was further passed through a sifting screen to get granules.

Step 11: The formed granules had a Loss on Drying (LOD) value of 7.76% w/w at one-hundred-five degrees Celsius (105° C.) over a period of nine (9) minutes and thirty-seven (37) seconds.

Step 12: The formed granules are uniformly mixed with the remaining quantity of the extra-granular blend from step 4 and further subjected to compression on rotary tablet press using 18 mm×18 mm rounded square punch for three gram (3 g) target fill weight.

Step 13: The compressed tablets exhibited tablets hardness of zero (0) newton or kilopond when measured using conventional hardness tester and had tablet friability of 0.02% w/w.

Texture analysis was performed using CT3 Texture Analyzer using TA/RT/KIT probe and 25,000 g load cell and 510 g trigger load, over 4 mm using 2 mm/s test speed and using data rate of 10 points/second. Load peaks were applied at 2 and 15 seconds. The results are plotted in FIG. 2.

TABLE 6

Tablet Characterization, Examples 2-4

| Test Parameters | Example 2 | Example 3 | Example 4 |
|---|---|---|---|
| Weight (g) | 0.500 | 3.0 | 3.0 |
| Shape | Square | Square | Square |
| Color | Light Brown | Yellow-Brown | Yellow-Brown |
| Dimension (mm) | — | 18 × 18 | 18 × 18 |
| Thickness (mm) | 4.00-5.00 | 7.00-8.00 | 8.00-9.00 |
| Disintegration Time (min) | — | 10.00-15.00 | 20.00-21.00 |
| Tablet Hardness (kp) | 16.00-18.00 | 0 | 0 |
| Tablet Hardness (N) | 170 | — | 0 |
| Tablet Friability (% w/w) | — | 0 | 0.02 |
| LOD at 105° C (% w/w) | 6.00-7.00 | — | 7.00-8.00 |

The results of a comparative dissolution study (in vitro analysis—multimedia dissolution testing) involving the tablets formed according to Examples 2 and 3 are tabulated in Tables 7 and 8, respectfully. The dissolution profiles of Examples 2 and 3 were compared to a reference drug and a marketed soft-chew, respectfully. A paddle apparatus (USP II Apparatus) rotating at 100 rpm was used. The dissolution medium consisted of a nine-hundred milliliter (900 ml) 0.1 M HCl solution.

TABLE 7

| Time Points (Minutes) | Reference Drug (Hard Chew) | Example 2 (Hard Chew) |
|---|---|---|
| 5 | 4.2 | 5 |
| 15 | 8.8 | 10 |
| 30 | 9.4 | 15 |
| 45 | 9.9 | 13 |
| 60 | 11.6 | 13 |
| 90 | 11.9 | 18 |
| 120 | 12.7 | 15 |

TABLE 8

| Time Points (Minutes) | Marketed Soft-Chew | Example 3 (Prototype Soft-Chew) |
|---|---|---|
| 5 | 17 | 12.5 |
| 15 | 28 | 24.0 |
| 30 | 33 | 32.0 |
| 45 | 37 | 32.1 |
| 60 | 34 | 33.2 |

TABLE 8-continued

| Time Points (Minutes) | Marketed Soft-Chew | Example 3 (Prototype Soft-Chew) |
|---|---|---|
| 90 | 35 | 30.5 |
| 120 | 36 | 30.6 |

The data in Tables 7 and 8 is presented graphically in FIG. 3.

The results of a comparative dissolution study (in vitro analysis—multimedia dissolution testing) involving the tablets formed according to Examples 2 and 3 are tabulated in Tables 9 and 10, respectfully. The dissolution profiles of Examples 2 and 3 were compared to a reference drug and a marketed soft-chew, respectfully. A paddle apparatus (USP II Apparatus) rotating at 100 rpm was used. The dissolution medium consisted of a nine-hundred milliliter (900 ml) acetate buffer solution, pH 4.5.

TABLE 9

| Time Points (Minutes) | Reference Drug (Hard Chew) | Example 2 (Hard Chew) |
|---|---|---|
| 5 | 5.8 | 13 |
| 15 | 14.5 | 24 |
| 30 | 19.4 | 32 |
| 45 | 21.2 | 33 |
| 60 | 24.0 | 33 |
| 90 | 25.5 | 34 |
| 120 | 25.5 | 34 |

TABLE 10

| Time Points (Minutes) | Marketed Soft-Chew | Example 3 (Prototype Soft-Chew) |
|---|---|---|
| 5 | 21 | 18.0 |
| 15 | 41 | 37.5 |
| 30 | 53 | 51.4 |
| 45 | 55 | 54.4 |
| 60 | 56 | 54.1 |
| 90 | 56 | 51.5 |
| 120 | 57 | 53.0 |

The data in Tables 9 and 10 is presented graphically in FIG. 4.

The results of a comparative dissolution study (in vitro analysis—multimedia dissolution testing) involving the tablets formed according to Examples 2 and 3 are tabulated in Tables 11 and 12, respectfully. The dissolution profiles of Examples 2 and 3 were compared to a reference drug and a marketed soft-chew, respectfully. A paddle apparatus (USP II Apparatus) rotating at 100 rpm was used. The dissolution medium consisted of a nine-hundred milliliter (900 ml) phosphate buffer solution, pH 7.5.

TABLE 11

| Time Points (Minutes) | Reference Drug (Hard Chew) | Example 2 (Hard Chew) |
|---|---|---|
| 5 | 23.8 | 26.00 |
| 15 | 59.2 | 68.00 |
| 30 | 90.8 | 92.00 |
| 45 | 93.2 | 92.00 |
| 60 | 93.6 | 92.00 |
| 90 | 93.7 | 92.00 |
| 120 | 94.1 | 93.00 |

TABLE 12

| Time Points (Minutes) | Marketed Soft-Chew | Example 3 (Prototype Soft-Chew) |
|---|---|---|
| 5 | 25.0 | 22.0 |
| 15 | 66.9 | 55.0 |
| 30 | 91.1 | 87.0 |
| 45 | 95.3 | 96.0 |
| 60 | 95.3 | 97.0 |
| 90 | 95.3 | 97.0 |
| 120 | 95.3 | 97.0 |

The data in Tables 11 and 12 is plotted in FIG. 5.

Ingredients corresponding to Examples 5-8 are tabulated in Table 13, with the amount of each ingredient given in respective percent by weight (% w/w).

TABLE 13

| Ingredients | Example 5 | Example 6 | Example 7 | Example 8 |
|---|---|---|---|---|
| Active | | | | |
| Cefpodoxime Proxetil | 13.50 | — | — | — |
| Enrofloxacin | — | 4.54 | — | — |
| Pimobendan | — | — | 0.08 | — |
| Deracoxib | — | — | — | 3.34 |
| Granulation Aid Ingredients | | | | |
| Soybean Oil | 7.00 | 9.00 | 10.00 | 15.00 |
| Zea Mays Oil & BHA & BHT | 0.10 | 0.10 | 0.10 | 0.10 |
| Glycerin | 20.00 | 13.00 | 12.00 | 19.50 |
| Polyethylene Glycol 600 | 3.00 | 9.00 | 10.20 | — |
| Povidone K 30 | 2.00 | 2.00 | 2.00 | 2.00 |
| Color | — | — | 0.01 | 0.02 |
| Intra-granular Ingredients | | | | |
| Polycarbophil | — | — | — | 0.25 |
| Lactose Monohydrate | — | — | — | — |
| Sodium Carboxymethylcellulose | 20.00 | — | — | — |
| Silicified Microcrystalline Cellulose | 3.85 | 18.15 | 18.71 | 15.59 |
| Sodium Lauryl Sulfate | 1.50 | — | — | — |
| Pregelatinized Corn Starch | 2.00 | 7.00 | 7.00 | 8.00 |
| Calcium Sulfate Dihydrate | — | 2.50 | 2.50 | 2.50 |
| Artificial Beef Flavor | 15.00 | 15.00 | 15.00 | 15.00 |
| Croscarmellose Sodium | 2.00 | 3.50 | — | 1.50 |
| Polyethylene Glycol 600 | — | — | 2.50 | 1.00 |
| Color | — | — | — | — |
| Polyethylene Glycol 3350 | — | — | — | — |
| Extra-granular Ingredients | | | | |
| Pregelatinized Corn Starch | — | 4.00 | 5.00 | 5.00 |
| Artificial Beef Flavor | 3.00 | 3.00 | 3.00 | 3.00 |
| Citric Acid | — | — | — | — |
| Sodium Carboxymethylcellulose | 5.00 | — | — | — |
| Sodium Lauryl Sulfate | — | 0.20 | 0.30 | 0.20 |
| Poly(ethylene) Oxide | — | 1.00 | 1.00 | 1.00 |
| Color | 0.05 | — | — | — |
| Modified Corn Starch | — | — | — | — |
| Croscarmellose | 2.00 | 1.50 | 2.50 | 5.00 |

TABLE 13-continued

| Ingredients | Example 5 | Example 6 | Example 7 | Example 8 |
|---|---|---|---|---|
| Sodium Calcium Sulfate Dihydrate | — | 2.01 | 1.70 | 1.00 |
| Lactose Monohydrate - | — | 4.50 | 6.50 | 1.00 |
| Total | 100.00 | 100.00 | 100.00 | 100.00 |

Procedure—Example 5

Step 1: Soybean oil and *Zea mays* oil and BHA and BHT are weighed accurately and uniformly mixed to form a dispersion.

Step 2: Simultaneously, a dispersion is prepared by adding polyethylene glycol 600 to glycerin and properly mixing.

Step 3: Cefpodoxime proxetil (active) was part of the intra-granular addition. All intra-granular dry ingredients were mixed uniformly and passed through sifting screen.

Step 4: The dispersions from Step 1 and Step 2 are used as granulation aid, adding them one after another to the pre-mixed ingredients from Step 3.

Step 5: The formed doughy mass was passed through a sifting screen to get wet granules.

Step 6: The extra-granular ingredients were mixed uniformly and passed through a sifting screen.

Step 7: Approximately half the quantity of the extra-granular blend from Step 6 was added to the wet granules formed in Step 5 and mixed uniformly.

Step 8: The formed slightly dry granular mass was passed through sifting screen to get granules.

Step 9: The formed granules were mixed uniformly with remaining quantity of extra-granular blend and further subjected to compression on rotary tablet press using 15.3 mm×15.3 mm rounded square punch for 2000 mg fill weight and 12.3 mm×12.3 mm rounded square for 1000 mg fill weight separately.

The results of a comparative dissolution study (in vitro analysis—multimedia dissolution testing) involving the tablets formed according to Example 5 are tabulated in Tables 14 and 15. The dissolution profile of Example 5 was compared to a reference drug. A paddle apparatus (USP II Apparatus) rotating at 75 rpm was used. The dissolution medium consisted of a nine-hundred milliliter (900 ml) glycine buffer solution, pH 3.0.

TABLE 14

| Time Points (Minutes) | Reference Drug 100 mg (Hard Chew) | Example 5 1000 mg (Soft-Chew) |
|---|---|---|
| 5 | 79.8 | 50.8 |
| 15 | 99.9 | 95.8 |
| 30 | 102.2 | 103.3 |
| 45 | 101.0 | 104.8 |

TABLE 15

| Time Points (Minutes) | Reference Drug 200 mg (Hard Chew) | Example 5 2000 mg (Soft-Chew) |
|---|---|---|
| 5 | 77.1 | 43.2 |
| 15 | 92.3 | 86.4 |

TABLE 15-continued

| Time Points (Minutes) | Reference Drug 200 mg (Hard Chew) | Example 5 2000 mg (Soft-Chew) |
|---|---|---|
| 30 | 98.0 | 99.0 |
| 45 | 98.4 | 103.0 |

The data in Tables 14 and 15 is plotted in FIG. 6.

Procedure—Examples 6-8

Step 1: The active, soybean oil and *Zea mays* oil and BHA and BHT were uniformly mixed to form a dispersion.

Step 2: Simultaneously, a dispersion was prepared by weighing the remaining granulation aid ingredients followed by properly mixing.

Step 3: Intra granular dry ingredients were uniformly mixed and passed through a sifting screen.

Step 4: The dispersions from Step 1 and Step 2 were used as a granulation aid, adding them one after another to pre-mixed ingredients from Step 3.

Step 5: The formed mass was passed through sifting screens to get wet granules.

Step 6: The extra-granular ingredients were mixed uniformly and passed through a sifting screen.

Step 7: Approximately half the quantity of the extra-granular blend from Step 6 was added to the wet granules formed in Step 5 and mixed uniformly.

Step 8: The formed slightly dry granular mass was passed through a sifting screen to obtain granules.

Step 9: The formed granules are uniformly mixed with remaining quantity of extra-granular blend and further subjected to compression on rotary tablet press.

The results of a comparative dissolution study (in vitro analysis—multimedia dissolution testing) involving the tablets formed according to Example 6 are tabulated in Table 16. The dissolution profile of Example 6 was compared to a reference drug. A paddle apparatus (USP II Apparatus) rotating at 100 rpm was used. The dissolution medium consisted of a nine-hundred milliliter (900 ml) citrate buffer solution, pH 4.0.

TABLE 16

| Time Points (Minutes) | Reference Drug (Hard Chew) | Example 6 (Soft-Chew) |
|---|---|---|
| 5 | 64.9 | 95.2 |
| 10 | 96.9 | 97.2 |
| 15 | 98.7 | 97.7 |
| 30 | 99.2 | 96.6 |
| 45 | 98.8 | 98.6 |

The data in Table 16 is plotted in FIG. 7.

Ingredients corresponding to Examples 9-11 (carprofen soft chewable tablets) are tabulated in Table 12, with the amount of each ingredient given in respective percent by weight (w/w %). In each of the Examples 9-11, the active ingredient is carprofen. In Example 9, the active strength of carprofen is about 25 mg. In Example 10, the active strength of carprofen is about 75 mg. In Example 11, the active strength of carprofen is about 100 mg.

TABLE 17

| Ingredient | Example 9 | Example 10 | Example 11 |
|---|---|---|---|
| Granulation Aid | | | |
| Carprofen | 0.83 | 2.5 | 3.33 |
| Mineral Oil | 8 | 8 | 8 |
| Sorbitol | 15.5 | 15.5 | 15.5 |
| Polyethylene Glycol (PEG-600) | 6 | 6 | 6 |
| Povidone (K-30) | 2.3 | 2.3 | 2.3 |
| Brown Iron Oxide | 0.01 | 0.01 | 0.01 |
| Intra-granular Ingredients | | | |
| Carnauba Wax | 5 | 4 | 4 |
| Silicified Microcrystalline Cellulose | 19.84 | 19.84 | 19.01 |
| Lactose | 3.92 | 3 | 3 |
| Pregelatinized Corn Starch | 2 | 2 | 2 |
| Calcium Sulfate Dihydrate | 2 | 2 | 2 |
| Croscarmellose sodium | 0.1 | 0.35 | 0.35 |
| Beef Flavor | 15 | 15 | 15 |
| Extra-granular Ingredients | | | |
| Pregelatinized Corn Starch | 5 | 5 | 5 |
| Silicified Microcrystalline Cellulose | 7.5 | 7.5 | 7.5 |
| Beef Flavor | 3 | 3 | 3 |
| Lactose | 2 | 2 | 2 |
| Flow Aid Ingredient | | | |
| Sodium Stearyl Fumarate | 2 | 2 | 2 |
| Total | 100 | 100 | 100 |

Procedure—Examples 9-11

Step 1: All intra-granular materials (silicified microcrystalline cellulose, carnauba wax, pregelatinized starch, beef flavor, croscarmellose sodium, calcium sulfate dihydrate) were passed through simultaneously through #40 mesh screen using mechanical sifter and once again passed through #40 mesh screen.

Step 2: All extra-granular materials (pregelatinized starch, lactose monohydrate, beef flavor and croscarmellose sodium) passed through simultaneously through #40 mesh screen and once again passed through #40 mesh screen and approximately divided into two parts (75% and 25%).

Step 3: Sodium stearyl fumarate passed through #40 mesh screen and once again passed through #40 mesh screen.

Step 4: Sorbitol and polyethylene glycol kept in a vessel under stirring.

Step 5: Povidone was added to materials from Step 4 under continuous stirring to obtain a clear, lump free dispersion.

Step 6: Brown iron oxide added to materials from Step 5 under continuous stirring to obtain a lump free dispersion.

Step 7: Carprofen was added to mineral oil under continuous stirring to obtain a lump free dispersion.

Step 8: Dispersion from Step 7 was added to materials from Step 1.

Step 9: Dispersion from Step 6 was added to materials Step 8 to form a wet mass.

Step 10: Wet mass of Step 9 was kneaded for up to two (2) minutes.

Step 11: Wet mass of Step 10 and approximately 75% materials of Step 2 were passed through cone-mill using six millimeter (6 mm) screen at slow speed and knife forward to form granules.

Step 12: Granules from Step 11 were further passed through #8 mesh screen to form final granules.

Step 13: Granules from Step 12 and remaining 25% material from Step 2 were blended together for three (3) minutes.

Step 14: Granules from Step 13 were lubricated with material from Step 3 for five (5) minutes.

Step 15: The formed granules were subjected to compression on rotary tablet press using 18 mm×18 mm rounded square punch.

Table 18: Tablet Characterization—Examples 9-11 compared to Marketed Product.

TABLE 18

| Parameters | Marketed Product | Example 9 | Example 10 | Example 11 |
|---|---|---|---|---|
| Weight (mg) | 3860 | 3000 | 3000 | 3000 |
| Shape | Trapezoidal | Rounded Square | Rounded Square | Rounded Square |
| Color | Brown | Light brown to brown | Light brown to brown | Light brown to brown |
| Width × Length Top (mm) | 16.4 × 17.1 | 18.0 × 18.0 | 18.0 × 18.0 | 18.0 × 18.0 |
| Width × Length Bottom (mm) | 17.8 × 18.6 | 18.0 × 18.0 | 18.0 × 18.0 | 18.0 × 18.0 |
| Thickness (mm) | 9.5 | 8.6 | 8.8 | 8.8 |
| Disintegration Time (min) | 26 | 20 | 24 | 26 |
| Hardness (N) | 0 | 0 | 0 | 0 |
| Friability (%) | 0 | 0 | 0 | 0 |

Table 19: Texture Analysis—Examples 9-11 compared to Marketed Product. Analysis performed using a CT3 Texture Analyzer (Brookfield Engineering) using a TA18 Probe and twenty-five-thousand gram (25,000 g) load cell and five gram (5 g) trigger load, over four millimeters (4 mm) using two millimeter per second (2 mm/s) test speed and using a data rate of twenty (20) points/second.

TABLE 19

| Parameters | Marketed Product | Example 9 | Example 10 | Example 11 |
|---|---|---|---|---|
| Hardness Cycle 1 (g) | 5886 | 636 | 2088 | 1806 |
| Hardness Cycle 2 (g) | 4610 | 130 | 202 | 414 |
| Deformation at hardness (mm) | 3.97 | 1.69 | 2.16 | 2.27 |
| Stringiness Length (mm) | 0.91 | 56.14 | 0.1 | 0 |
| Adhesiveness (mJ) | 0.1 | 0.4 | 0.7 | 0 |
| Cohesiveness | 0.46 | 0.02 | 0.03 | 0.41 |
| Gumminess (g) | 2703 | 10 | 59 | 744 |
| Chewiness (mJ) | 74.7 | 0.2 | 1.7 | 355.5 |
| Springiness | 2.82 | 2.23 | 2.87 | 48.71 |

The results of a comparative dissolution study involving the tablets formed according to Examples 9-11 are tabulated in Tables 20-22, respectively. The dissolution profiles of Examples 9-11 were compared to marketed products having similar active strengths. A paddle apparatus rotating at 100 rpm was used. Nine-hundred milliliters (900 ml) of phosphate buffer pH 7.5 was used as the dissolution medium.

TABLE 20

| Time point | Marketed product 25 mg | Example 9 |
|---|---|---|
| 0 | 0 | 0 |
| 5 | 20 | 27 |
| 15 | 55 | 67 |
| 30 | 89 | 90 |
| 45 | 98 | 96 |
| 60 | 98 | 98 |
| 90 | 98 | 98 |
| 120 | 98 | 98 |

TABLE 21

| Time point | Marketed product 75 mg | Example 10 |
|---|---|---|
| 0 | 0 | 0 |
| 5 | 16 | 19 |
| 15 | 44 | 51 |
| 30 | 76 | 77 |
| 45 | 88 | 91 |
| 60 | 93 | 96 |
| 90 | 93 | 98 |
| 120 | 93 | 98 |

TABLE 22

| Time point | Marketed product 100 mg | Example 11 |
|---|---|---|
| 0 | 0 | 0 |
| 5 | 14 | 16 |
| 15 | 42 | 45 |
| 30 | 73 | 71 |
| 45 | 89 | 87 |
| 60 | 91 | 93 |
| 90 | 92 | 97 |
| 120 | 92 | 97 |

Ingredients corresponding to Examples 12-14 (carprofen soft chewable tablets) are tabulated in Table 23, with the amount of each ingredient given in respective percent by weight (% w/w). In each of the Examples 12-14, the active ingredient is carprofen. In Example 12, the active strength of carprofen is about 25 mg. In Example 13, the active strength of carprofen is about 75 mg. In Example 14, the active strength of carprofen is about 100 mg.

TABLE 23

| Ingredients | Example 12 | Example 13 | Example 14 |
|---|---|---|---|
| Granulation Aid Ingredients | | | |
| Mineral Oil | 8 | 8 | 8 |
| Sorbitol | 15.5 | 15.5 | 15.5 |
| Polyethylene Glycol (PEG 600) | 3.5 | 3.5 | 4 |
| Povidone (K-30) | 0.5 | 0.2 | 0.4 |
| Brown Iron Oxide | 0.01 | 0.01 | 0.01 |
| Intra-granular Ingredients | | | |
| Carprofen | 0.83 | 2.5 | 3.33 |
| Carnauba wax | 4 | 4 | 4 |
| Lactose | 20.31 | 20.09 | 17.41 |
| Silicified Microcrystalline Cellulose | 7.6 | 7.6 | 7.6 |
| Pregelatinized Corn Starch | 2 | 2 | 2 |
| Calcium Sulfate Dihydrate | 2 | 2 | 2 |
| Croscarmellose Sodium | 0.25 | 0.6 | 0.25 |
| Beef Flavor | 15 | 15 | 15 |
| Extra-granular Ingredients | | | |
| Pregelatinized Corn Starch | 5 | 5 | 5 |
| Silicified Microcrystalline Cellulose | 7.5 | 7 | 7.5 |
| Beef Flavor | 3 | 3 | 3 |
| Lactose | 3 | 2 | 3 |
| Flow Aid Ingredient | | | |
| Sodium Stearyl Fumarate | 2 | 2 | 2 |
| Total | 100 | 100 | 100 |

Procedure—Examples 12-14

Step 1: All intra-granular materials (carprofen, carnauba wax, lactose monohydrate, silicified microcrystalline cellulose, pregelatinized starch, calcium sulphate dihydrate, beef flavor and croscarmellose sodium) were passed simultaneously through #40 mesh followed by mixing.

Step 2: All extra-granular materials (lactose monohydrate, silicified microcrystalline cellulose, pregelatinized starch and beef flavor) were passed simultaneously through #40 mesh screen and approximately divided into two parts (75% and 25%).

Step 3: Sodium stearyl fumarate was passed through #40 mesh screen.

Step 4: Povidone was added to sorbitol and polyethylene glycol under continuous stirring to get clear solution.

Step 5: Brown iron oxide was added to dispersion from Step 4 under continuous stirring.

Step 6: Materials from Step 4 were added to the materials from Step 1 and mixed continuously until uniformly mixed, followed by addition of mineral oil and mixing continuously to get granulated wet mass.

Step 7: Wet mass from Step 6 was passed through multi-mill using six millimeter (6 mm) screen to form granules.

Step 8: 75% of the quantity of extra-granular materials from Step 2 and granules from Step 8 were passed through #8 mesh screen.

Step 9: Remaining quantity of extra-granular materials (25%) from Step 2 and granules from Step 9 were blended together for two (2) minutes.

Step 10: Sodium stearyl fumarate from Step 3 was added to granules from Step 10 and blended together for two (2) minutes.

Step 11: The formed granules from Step 10 were subjected to compression on rotary tablet press using 18 mm×18 mm rounded square punch.

Table 24: Tablet Characterization—Examples 12-14

TABLE 24

| Parameters | Example 12 | Example 13 | Example 14 |
|---|---|---|---|
| Weight (mg) | 3000 | 3000 | 3000 |
| Shape | Rounded Square | Rounded Square | Rounded Square |
| Color | Light brown to brown | Light brown to brown | Light brown to brown |
| Width × Length Top (mm) | 18.0 × 18.0 | 18.0 × 18.0 | 18.0 × 18.0 |
| Width × Length Bottom (mm) | 18.0 × 18.0 | 18.0 × 18.0 | 18.0 × 18.0 |
| Thickness (mm) | 8.6 | 8.7 | 8.8 |

TABLE 24-continued

| Parameters | Example 12 | Example 13 | Example 14 |
|---|---|---|---|
| Disintegration Time (min) | 20 | 18 | 25 |
| Hardness (N) | 0 | 0 | 0 |
| Friability (%) | 0 | 0 | 0 |

The results of a texture analysis of the tablets formed according to Examples 12-14 are tabulated in Table 25. The texture analysis was performed using a CT3 Texture Analyzer (Brookfield Engineering) using a TA18 Probe and twenty-five-thousand gram (25,000 g) load cell and five gram (5 g) trigger load, over four millimeters (4 mm) using two millimeter per second (2 mm/s) test speed and using a data rate of twenty (20) points/second.

TABLE 25

| Parameters | Example 12 | Example 13 | Example 14 |
|---|---|---|---|
| Hardness Cycle 1 (g) | 1310 | 1900 | 1434 |
| Hardness Cycle 2 (g) | 276 | 238 | 156 |
| Deformation at hardness (mm) | 1.58 | 1.67 | 1.68 |
| Stringiness Length (mm) | 64.2 | 69.26 | 22.53 |
| Adhesiveness (mJ) | 1.1 | 0.6 | 0.5 |
| Cohesiveness | 0 | 0.03 | 0.1 |
| Gumminess (g) | −1 | 58 | 149 |
| Chewiness (mJ) | 0 | 1.6 | 5 |
| Springiness | 0.92 | 2.75 | 3.45 |

Tables 26-28 show the results accelerated stability study of the tablets formed according to Examples 12-14, respectively. The tablets were packaged in a high-density polyethylene (HDPE) container and stored at a temperature of 40° C.±2° C. and a relative humidity (RH) of 75%±5%.

TABLE 26

| Stability Parameters | Initial | 1-Month | 3-Months |
|---|---|---|---|
| Loss On Drying (LOD) at 105° C. | 5.66 | 6.64 | 6.71 |
| Assay (%) | 96.6 | 97.4 | 95.9 |
| Dissolution (%) | 99 | 98 | 93 |
| Related Substances (%) | 0.078 / 0.145 | ND / 0.14 | 0.14 / 0.21 |

TABLE 27

| Stability Parameters | Initial | 1-Month | 3-Months |
|---|---|---|---|
| Loss On Drying (LOD) at 105° C. | 7.12 | 7.01 | 7.14 |
| Assay (%) | 98.8 | 100.3 | 99 |
| Dissolution (%) | 94 | 94 | 88 |
| Related Substances (%) | 0.082 / 0.198 | ND / 0.17 | 0.19 / 0.25 |

TABLE 28

| Stability Parameters | Initial | 1-Month | 3-Months |
|---|---|---|---|
| Loss On Drying (LOD) at 105° C. | 7.2 | 6.89 | 6.68 |
| Assay (%) | 94.2 | 99.6 | 97.6 |
| Dissolution (%) | 92 | 76 | 83 |
| Related Substances (%) | 0.074 / 0.173 | ND / 0.14 | 0.15 / 0.22 |

Ingredients corresponding to Example 15 are tabulated in Table 29. The active ingredient in the formulation of Example 15 is enrofloxacin. The active strength of enrofloxacin used in the Example 15 formulation was 22.7 mg or 68 mg or 136 mg.

TABLE 29

| Ingredient | % wt./wt |
|---|---|
| Granulation Aid Ingredients | |
| Mineral Oil | 7 |
| Glycerin | 18 |
| Polyethylene Glycol (PEG-600) | 1.5 |
| Povidone (K-30) | 0.15 |
| Brown Iron Oxide | 0.01 |
| Intra-granular Ingredients | |
| Enrofloxacin | 4.53 |
| Carnauba wax | 4 |
| Lactose | 8.5 |
| Silicified Microcrystalline Cellulose | 15.21 |
| Calcium Sulfate Dihydrate | 2 |
| Beef Flavor | 15 |
| Croscarmellose Sodium | 4.5 |
| Extra-granular Ingredients | |
| Pregelatinized Starch | 3 |
| Silicified Microcrystalline Cellulose | 2.5 |
| Beef Flavor | 3 |
| Croscarmellose Sodium | 6.9 |
| Lactose | 2 |
| Flow Aid Ingredients | |
| Sodium Stearyl Fumarate | 2 |
| Sodium Lauryl Sulphate | 0.2 |
| Total | 100 |

Procedure—Example 15

Step 1: Intra-granular ingredients (enrofloxacin, silicified microcrystalline cellulose, carnauba wax, pregelatinized starch, beef flavor, croscarmellose sodium, and calcium sulphate dihydrate) were passed through simultaneously through #40 mesh screen and once again passed through #40 mesh screen followed by mixing.

Step 2: Extra-granular ingredients (pregelatinized starch, beef flavor, silicified microcrystalline cellulose, lactose and croscarmellose sodium) were passed through simultaneously through #40 mesh screen using mechanical sifter and resifted once through #40 mesh screen and approximately divided into two parts (75% and 25%).

Step 3: Sodium stearyl fumarate and sodium lauryl sulphate passed through simultaneously through #40 mesh screen and again passed through #40 mesh screen.

Step 4: Glycerin and polyethylene glycol were mixed in a vessel under stirring to form dispersion.

Step 5: Povidone was added to dispersion from Step 4 under continuous stirring to obtain a clear, lump free dispersion.

Step 6: Brown iron oxide added to dispersion from Step 5 under continuous stirring to obtain a lump free dispersion.

Step 7: Mineral oil was added to materials from Step 1.

Step 8: Dispersion from Step 6 was added to contents from Step 7 to form a wet mass.

Step 9: Wet mass from Step 8 was kneaded for up to one (1) minute.

Step 10: Wet mass from Step 9 and 75% extra-granular materials from Step 2 were passed simultaneously through cone-mill using six millimeter (6 mm) screen at slow speed and knife forward to form granules.

Step 11: Granules from Step 10 were further sifted by passing through #8 mesh screen.

Step 12: Granules from Step 11 and remaining 25% extra-granular materials from Step 2 were blended together for 3 minutes.

Step 13: Sodium Stearyl Fumarate and Sodium Lauryl sulphate from Step 3 were added to final granules from Step 12 and mixed together for 2 minutes.

Step 14: Compression was done using following tooling on a rotary tablet press. With respect to the Example 15 formulation having a enrofloxacin strength of 22.7 mg, a 10.5 mm×10.5 mm rounded square shape punch was used to compress a tablet having a 500 mg fill weight. With respect to the Example 15 formulation having a enrofloxacin strength of 68 mg, a 15.3 mm×15.3 mm rounded square shape punch was used to compress a tablet having a 1500 mg fill weight. With respect to the Example 15 formulation having a enrofloxacin strength of 136 mg, an 18.0 mm×18.0 mm rounded square shape punch was used to compress a tablet having a 3000 mg fill weight.

Table 23: Tablet Characterization—Example 15

TABLE 30

| Parameters | Example 15 22.7 mg | Example 15 68 mg | Example 15 136 mg |
| --- | --- | --- | --- |
| Weight (mg) | 500 | 1500 | 3000 |
| Shape | Rounded Square | Rounded Square | Rounded Square |
| Color | Light brown to brown | Light brown to brown | Light brown to brown |
| Area - Top (mm) Width × Length | 10.5 × 10.5 | 15.3 × 15.3 | 18.0 × 18.0 |
| Area - Bottom (mm) Width × Length | 10.5 × 10.5 | 15.3 × 15.3 | 18.0 × 18.0 |
| Thickness (mm) | 4.5 | 6.8 | 9 |
| Disintegration Time (min) | 5 min | 7 min | 9 min |
| Hardness (N) | 0 | 0 | 0 |
| Friability (%) | 0 | 0 | 0 |

The results of a texture analysis of the tablets formed according to Example 15 are tabulated in Table 31. The texture analysis was performed using a CT3 Texture Analyzer (Brookfield Engineering) using a TA18 Probe and twenty-five-thousand gram (25,000 g) load cell and five gram (5 g) trigger load, over four millimeters (4 mm) using two millimeter per second (2 mm/s) test speed and using a data rate of twenty (20) points/second.

TABLE 31

| Parameters | Example 15 22.7 mg | Example 15 68.0 mg | Example 15 136 mg |
| --- | --- | --- | --- |
| Hardness Cycle 1 (g) | 3348 | 1994 | 3142 |
| Hardness Cycle 2 (g) | 1186 | 232 | 6 |
| Deformation at hardness (mm) | 3.97 | 0.96 | 1.27 |
| Stringiness Length (mm) | 0 | 50.37 | 0 |
| Adhesiveness (mJ) | 0 | −0.1 | 0 |
| Cohesiveness | 0.03 | 0.09 | 0 |
| Gumminess (g) | 116 | 185 | 0 |

TABLE 31-continued

| Parameters | Example 15 22.7 mg | Example 15 68.0 mg | Example 15 136 mg |
| --- | --- | --- | --- |
| Chewiness (mJ) | 1.1 | 122.8 | 0 |
| Springiness | 0.25 | 67.84 | 1 |

The results of a comparative dissolution study involving the tablets formed according to Example 15 are tabulated in Tables 32-34. The dissolution profiles of Example 15 were compared to marketed products having similar active strengths. A paddle apparatus rotating at 100 rpm was used. Nine-hundred milliliters (900 ml) of pH 4.0 citrate buffer was used as the dissolution medium.

TABLE 32

| Time point | Marketed product 22.7 mg | Example 15 22.7 mg |
| --- | --- | --- |
| 0 | 0 | 0 |
| 5 | 71 | 64 |
| 10 | 99 | 90 |
| 15 | 99 | 99 |
| 30 | 99 | 99 |
| 45 | 99 | 99 |

TABLE 33

| Time point | Marketed product 68 mg | Example 15 68 mg |
| --- | --- | --- |
| 0 | 0 | 0 |
| 5 | 48 | 59 |
| 10 | 82 | 82 |
| 15 | 97 | 95 |
| 30 | 97 | 98 |
| 45 | 97 | 98 |

TABLE 34

| Time point | Marketed product 100 mg | Example 15 100 mg |
| --- | --- | --- |
| 0 | 0 | 0 |
| 5 | 45 | 45 |
| 10 | 70 | 68 |
| 15 | 89 | 81 |
| 30 | 98 | 98 |
| 45 | 98 | 99 |

Ingredients corresponding to Examples 16-18 are tabulated in Table 35, with the amount of each ingredient given in respective percent by weight (w/w %). In each of the Examples 16-18, the active ingredient is enrofloxacin. In Example 16, the active strength of enrofloxacin is about 22.7 mg. In Example 17, the active strength of enrofloxacin is about 68 mg. In Example 18, the active strength of enrofloxacin is about 136 mg.

TABLE 35

| Ingredient | Example 16 | Example 17 | Example 18 |
|---|---|---|---|
| Granulation Aid Ingredients | | | |
| Mineral Oil | 7 | 7 | 7 |
| Glycerin | 16 | 14 | 16 |
| Polyethylene Glycol (PEG-600) | 4 | 6 | 4 |
| Povidone (K-30) | 0.25 | 0.25 | 0.25 |
| Brown Iron Oxide | 0.01 | 0.01 | 0.01 |
| Intra-granular Ingredients | | | |
| Enrofloxacin | 4.53 | 4.53 | 4.53 |
| Carnauba wax | 4 | 6 | 4 |
| Lactose | 15.21 | 13.71 | 15.21 |
| Silicified Microcrystalline Cellulose | 8.5 | 8 | 8.5 |
| Calcium Sulfate Dihydrate | 2 | 2 | 2 |
| Beef Flavor | 15 | 15 | 15 |
| Croscarmellose Sodium | 4.5 | 4.5 | 4.5 |
| Extra-granular Ingredients | | | |
| Pregelatinized Starch | 3 | 3 | 3 |
| Silicified Microcrystalline Cellulose | 6.3 | 6.3 | 6.3 |
| Beef Flavor | 3 | 3 | 3 |
| Croscarmellose Sodium | 4.5 | 4.5 | 4.5 |
| Flow Aid Ingredients | | | |
| Sodium Stearyl Fumarate | 2 | 2 | 2 |
| Sodium Lauryl Sulphate | 0.2 | 0.2 | 0.2 |
| Total | 100 | 100 | 100 |

Procedure—Examples 16-18

Step 1: All intra-granular materials (enrofloxacin, carnauba wax, lactose monohydrate, silicified microcrystalline cellulose, calcium sulphate dihydrate, beef flavor and croscarmellose sodium) were passed through #40 mesh screen and mixed further.

Step 2: All extra-granular materials (pregelatinized starch, silicified microcrystalline cellulose, croscarmellose sodium and beef flavor) were passed through #40 mesh screen and approximately divided into two equal parts.

Step 3: Sodium stearyl fumarate and sodium lauryl sulphate were passed through #40 mesh screen and mixed further.

Step 4: Povidone was added to glycerin and polyethylene glycol under continuous stirring to get clear dispersion.

Step 5: Brown iron oxide was further added to dispersion from Step 4 under continuous stirring to get lump free dispersion.

Step 6: Final contents from Step 5 were added to the contents from Step 1 and mixed thoroughly followed by addition of mineral oil and mixing thoroughly to form wet mass.

Step 7: Wet mass from Step 6 was passed through multi-mill using six millimeter (6 mm) screen to form granules.

Step 8: Approximately half quantity of extra-granular contents from Step 2 and granules of Step 7 were passed though simultaneously #8 mesh screen.

Step 9: Remaining half quantity of extra-granular contents from Step 2 and granules from of Step 8 were mixed together for one (1) minute.

Step 10: Materials from Step 3 were added to granule from Step 9 and mixed together for one (1) minute.

Step 11: Compression was done using tooling on a rotary tablet press. With respect to Example 16, a 10.5 mm×10.5 mm rounded square shape punch was used to compress a tablet having a 500 mg fill weight. With respect to Example 17, a 15.3 mm×15.3 mm rounded square shape punch was used to compress a tablet having a 1500 mg fill weight. With respect to Example 18, an 18.0 mm×18.0 mm rounded square shape punch was used to compress a tablet having a 3000 mg fill weight.

Table 36: Tablet Characterization—Examples 16-18

TABLE 36

| Parameters | Example 16 | Example 17 | Example 18 |
|---|---|---|---|
| Weight (mg) | 500 | 1500 | 3000 |
| Shape | Rounded Square | Rounded Square | Rounded Square |
| Color | Light brown to brown | Light brown to brown | Light brown to brown |
| Width × Length Top (mm) | 10.5 × 10.5 | 14.5 × 14.5 | 18.0 × 18.0 |
| Width × Length Bottom (mm) | 10.5 × 10.5 | 15.3 × 15.3 | 18.0 × 18.0 |
| Thickness (mm) | 4.5 | 6.6 | 8.9 |
| Disintegration Time (min) | 5 min | 15 min | 10 min |
| Hardness (N) | 0 | 0 | 0 |
| Friability (%) | 0 | 0 | 0 |

The results of a texture analysis of the tablets formed according to Examples 16-18 are tabulated in Table 37. The texture analysis was performed using a CT3 Texture Analyzer (Brookfield Engineering) using a TA18 Probe and twenty-five-thousand gram (25,000 g) load cell and five gram (5 g) trigger load, over four millimeters (4 mm) using two millimeter per second (2 mm/s) test speed and using a data rate of twenty (20) points/second.

TABLE 37

| Parameters | Example 16 | Example 17 | Example 18 |
|---|---|---|---|
| Hardness Cycle 1 (g) | 2966 | 1068 | 1496 |
| Hardness Cycle 2 (g) | 1060 | 186 | 146 |
| Deformation at hardness (mm) | 3.97 | 1.2 | 1.79 |
| Stringiness Length (mm) | 66.02 | 70.16 | 48.86 |
| Adhesiveness (mJ) | 1.1 | 0.5 | −0.1 |
| Cohesiveness | 0.01 | −0.1 | 0.06 |
| Gumminess (g) | 16 | −8 | 91 |
| Chewiness (mJ) | 0.1 | −0.1 | 53.3 |
| Springiness | 0.76 | 0.89 | 59.89 |

Tables 38-40 show the results accelerated stability study of the tablets formed according to Examples 16-18, respectively. The tablets were packaged in a high-density polyethylene (HDPE) container and stored at a temperature of 40. C±2. C and a relative humidity (RH) of 75%±5%.

TABLE 38

| Stability Parameters | Initial | 1-Month | 3-Months |
|---|---|---|---|
| Loss On Drying (LOD) at 105° C. | 7.6 | 10.82 | 10.2 |
| Assay (%) | 101.6 | 101.8 | 98.4 |
| Dissolution (%) | 105.2 | 103.4 | 106 |
| Related Substances (%) | 0.147 | 0.077 | 0.13 |
| | 0.22 | 0.286 | 0.26 |

TABLE 39

| Stability Parameters | Initial | 1-Month | 3-Months |
|---|---|---|---|
| Loss On Drying (LOD) at 105° C. | 8.1 | 9.42 | 9 |
| Assay (%) | 98.9 | 100 | 98.5 |
| Dissolution (%) | 103.4 | 99.5 | 102 |
| Related Substances (%) | 0.15 | 0.073 | 0.18 |
| | 0.22 | 0.272 | 0.31 |

TABLE 40

| Stability Parameters | Initial | 1-Month | 3-Months |
|---|---|---|---|
| Loss On Drying (LOD) at 105° C. | 7.6 | 12.01 | 11.03 |
| Assay (%) | 100.1 | 100 | 99 |
| Dissolution (%) | 100.8 | 98 | 100 |
| Related Substances (%) | 0.135 | 0.074 | 0.2 |
| | 0.207 | 0.272 | 0.33 |

Ingredients corresponding to Examples 19-23 are tabulated in Table 41, with the amount of each ingredient given in respective percent by weight (w/w %). In each of the Examples 19-23, the active ingredient is deracoxib. In Example 19, the active strength of deracoxib is about 12 mg. In Example 20, the active strength of deracoxib is about 25 mg. In Example 21, the active strength of deracoxib is about 50 mg. In Example 22, the active strength of deracoxib is about 75 mg. In Example 23, the active strength of deracoxib is about 100 mg.

TABLE 41

| Ingredient | Example 19 | Example 20 | Example 21 | Example 22 | Example 23 |
|---|---|---|---|---|---|
| Granulation Aid Ingredients | | | | | |
| Mineral Oil | 8 | 8 | 8 | 8 | 8 |
| Sorbitol | 15.5 | 15.5 | 15.5 | 15.5 | 15.5 |
| Polyethylene Glycol (PEG-600) | 3.5 | 3.5 | 3.5 | 3.5 | 3.5 |
| Povidone (K-30) | 0.2 | 0.2 | 0.2 | 0.2 | 0.2 |
| Brown Iron Oxide | 0.01 | 0.01 | 0.01 | 0.01 | 0.01 |
| Intra-granular Ingredients | | | | | |
| Deracoxib | 3.33 | 3.33 | 3.33 | 3.33 | 3.33 |
| Carnauba Wax | 4 | 4 | 4 | 4 | 4 |
| Lactose Monohydrate | 17.1 | 17.1 | 17.1 | 17.1 | 17.1 |
| Silicified Microcrystalline Cellulose | 6.4 | 6.4 | 6.4 | 6.4 | 6.4 |
| Pregelatinized Starch | 1 | 1 | 1 | 1 | 1 |
| Calcium Sulfate Dihydrate | 2 | 2 | 2 | 2 | 2 |
| Beef Flavor | 15 | 15 | 15 | 15 | 15 |
| Croscarmellose Sodium | 5 | 5 | 5 | 5 | 5 |
| Extra-granular Ingredients | | | | | |
| Lactose Monohydrate | 5 | 2 | 5 | 7 | 5 |
| Silicified Microcrystalline Cellulose | 5.86 | 5.86 | 5.86 | 5.86 | 5.86 |
| Beef Flavor | 3 | 3 | 3 | 3 | 3 |
| Croscarmellose Sodium | 3 | 6 | 3 | 1 | 3 |
| Flow Aid Ingredients | | | | | |
| Sodium Stearyl Fumarate | 2 | 2 | 2 | 2 | 2 |
| Sodium Lauryl Sulphate | 0.1 | 0.1 | 0.1 | 0.1 | 0.1 |
| Total | 100 | 100 | 100 | 100 | 100 |

Procedure—Examples 19-23

Step 1: All intra-granular materials (deracoxib, carnauba wax, lactose monohydrate, silicified microcrystalline cellulose, pregelatinized starch, calcium sulphate dihydrate, beef flavor and croscarmellose sodium) were passed simultaneously through #40 mesh screen and mixed further.

Step 2: All extra-granular materials (lactose monohydrate, silicified microcrystalline cellulose, croscarmellose sodium and beef flavor) were passed simultaneously through #40 mesh screen and mixed further and divided into approximately two parts (75% and 25%).

Step 3: Sodium stearyl fumarate and sodium lauryl sulphate were passed simultaneously through #40 mesh and mixed further.

Step 4: Povidone was added into sorbitol and polyethylene glycol under continuous stirring to get clear dispersion.

Step 5: Brown iron oxide was added to dispersion from Step 4 under continuous stirring to get lump free dispersion.

Step 6: All granulation aid components except mineral oil were added to the contents from step 1 and mixed thoroughly until uniformly mixed, followed by quick addition of mineral oil followed by mixing thoroughly to form wet mass.

Step 7: Wet mass from Step 6 was passed through multi-mill using six millimeter (6 mm) screen to form granules.

Step 8: Approximately 75% quantity of extra-granular materials from Step 2 and granules of Step 7 were passed through #8 mesh screen using vibro-sifter.

Step 9: Remaining quantity of extra-granular materials (25%) from Step 2 and sifted granules of Step 8 were mixed together for two (2) minutes.

Step 10: Materials from Step 3 were added to granules from Step 10 and mixed together for two (2) minutes.

Step 11: Final granules from Step 10 were compressed using following punches on rotary tablet press. With respect to Example 19, an 8.0 mm×8.0 mm rounded square shape punch was used to compress a tablet having a 360 mg fill weight. With respect to Example 20, a 12.3 mm×12.3 mm rounded square shape punch was used to compress a tablet having a 750 mg fill weight. With respect to Example 21, a 15.3 mm×15.3 mm rounded square shape punch was used to compress a tablet having a 1500 mg fill weight. With respect to Example 22, a 17.0 mm×17.0 mm rounded square shape punch was used to compress a tablet having a 2250 mg fill weight. With respect to Example 23, an 18.0 mm×18.0 mm rounded square shape punch was used to compress a tablet having a 3000 mg fill weight.

Table 42: Tablet Characterization—Examples 19-23

TABLE 42

| Parameters | Example 19 | Example 20 | Example 21 | Example 22 | Example 23 |
| --- | --- | --- | --- | --- | --- |
| Weight (mg) | 360 | 750 | 1500 | 2250 | 3000 |
| Shape | Rounded Square | Rounded Square | Rounded Square | Rounded Square | Rounded Square |
| Color | Light brown to brown | Light brown to brown | Light brown to brown | Light brown to brown | Light brown to brown |
| Width × Length Top (mm) | 8.0 × 8.0 | 12.3 × 12.3 | 15.3 × 15.3 | 17.0 × 17.0 | 18.0 × 18.0 |
| Width × Length Bottom (mm) | 8.0 × 8.0 | 12.3 × 12.3 | 15.3 × 15.3 | 17.0 × 17.0 | 18.0 × 18.0 |
| Thickness(mm) | 5.3 | 4.9 | 6.2 | 7.5 | 8.9 |
| Disintegration Time (min) | 7 min | 4 min | 6 min | 10 min | 8 min |
| Hardness (N) | 0 | 0 | 0 | 0 | 0 |
| Friability (%) | 0 | 0 | 0 | 0 | 0 |

The results of a texture analysis of the tablets formed according to Examples 19-23 are tabulated in Table 43. The texture analysis was performed using a CT3 Texture Analyzer (Brookfield Engineering) using a TA18 Probe and twenty-five-thousand gram (25,000 g) load cell and five gram (5 g) trigger load, over four millimeters (4 mm) using two millimeter per second (2 mm/s) test speed and using a data rate of twenty (20) points/second.

TABLE 43

| Parameters | Example 19 | Example 20 | Example 21 | Example 22 | Example 23 |
| --- | --- | --- | --- | --- | --- |
| Hardness Cycle 1 (g) | 1890 | 5904 | 1764 | 1768 | 2866 |
| Hardness Cycle 2 (g) | 744 | 1886 | 242 | 162 | 180 |
| Deformation at hardness (mm) | 3.99 | 3.94 | 1.59 | 1.68 | 1.78 |
| Stringiness Length (mm) | 62.17 | 0 | 7.88 | 0 | 0 |
| Adhesiveness (mJ) | 0 | 1.5 | 0.1 | 0.6 | −0.1 |
| Cohesiveness | 0.04 | 0.01 | 0.03 | 0.01 | 0.03 |
| Gumminess (g) | 83 | 62 | 45 | 24 | 81 |
| Chewiness (mJ) | 0.8 | 0.4 | 0.6 | 0.7 | 42.2 |
| Springiness | 0.99 | 0.68 | 1.28 | 3.09 | 52.88 |

The results of a comparative dissolution study involving the tablets formed according to Examples 19-23 are tabulated in Tables 44-48, respectfully. The dissolution profiles of Examples 19-23 were compared to a marketed products having similar active strengths. A paddle apparatus rotating at 75 rpm. Nine-hundred milliliters (900 ml) of pH 12.4 phosphate buffer with 1% SLS was used as the dissolution medium.

TABLE 44

| Time point | Marketed Product 12 mg | Example 19 |
|---|---|---|
| 0 | 0 | 0 |
| 5 | 57 | 76 |
| 10 | 88 | 100 |
| 15 | 96 | 103 |
| 30 | 97 | 104 |
| 45 | 96 | 104 |

TABLE 45

| Time point | Marketed Product 25 mg | Example 20 |
|---|---|---|
| 0 | 0 | 0 |
| 5 | 46 | 46 |
| 10 | 77 | 74 |
| 15 | 92 | 90 |
| 30 | 97 | 98 |
| 45 | 97 | 99 |

TABLE 46

| Time point | Example 21 |
|---|---|
| 0 | 0 |
| 5 | 46 |
| 10 | 69 |
| 15 | 87 |
| 30 | 98 |
| 45 | 98 |

TABLE 47

| Time point | Marketed Product 75 mg | Example 22 |
|---|---|---|
| 0 | 0 | 0 |
| 5 | 34 | 37 |
| 10 | 53 | 61 |
| 15 | 66 | 77 |
| 30 | 75 | 98 |
| 45 | 87 | 100 |

TABLE 48

| Time point | Marketed Product 100 mg | Example 23 |
|---|---|---|
| 0 | 0 | 0 |
| 5 | 37 | 26 |
| 10 | 56 | 50 |
| 15 | 71 | 68 |
| 30 | 82 | 92 |
| 45 | 95 | 96 |

Tables 49-53 show the results accelerated stability study of the tablets formed according to Examples 19-23, respectively. The tablets were packaged in a high-density polyethylene (HDPE) container and stored at a temperature of 40° C.±2. C and a relative humidity (RH) of 75%±5%.

TABLE 49

| Stability Parameters | Initial | 1-Month | 3-Months |
|---|---|---|---|
| Loss On Drying (LOD) at 105° C. | 12.97 | 9.24 | 8.95 |
| Assay (%) | 102.8 | 100.9 | 99.6 |
| Dissolution (%) | 104 | 100 | 102 |
| Related | ND | ND | ND |
| Substances (%) | ND | ND | ND |

TABLE 50

| Stability Parameters | Initial | 1-Month | 3-Months |
|---|---|---|---|
| Loss On Drying (LOD) at 105° C. | 9.52 | 8.2 | 8.5 |
| Assay (%) | 103.4 | 100.9 | 98.7 |
| Dissolution (%) | 99 | 100 | 104 |
| Related | ND | ND | ND |
| Substances (%) | ND | ND | ND |

TABLE 51

| Stability Parameters | Initial | 1-Month | 3-Months |
|---|---|---|---|
| Loss On Drying (LOD) at 105° C. | 12.97 | 10.14 | 7.26 |
| Assay (%) | 99.2 | 100.5 | 96.7 |
| Dissolution (%) | 97 | 96 | 92 |
| Related | ND | ND | ND |
| Substances (%) | ND | ND | ND |

TABLE 52

| Stability Parameters | Initial | 1-Month | 3-Months |
|---|---|---|---|
| Loss On Drying (LOD) at 105° C. | 8.24 | 10.11 | 6.89 |
| Assay (%) | 98.4 | 101.5 | 99.9 |
| Dissolution (%) | 100 | 93 | 99 |
| Related | ND | ND | ND |
| Substances (%) | ND | ND | ND |

TABLE 53

| Stability Parameters | Initial | 1-Month | 3-Months |
|---|---|---|---|
| Loss On Drying (LOD) at 105° C. | 12.97 | 10.02 | 8.23 |
| Assay (%) | 103.3 | 100.6 | 100.9 |
| Dissolution (%) | 97 | 89 | 92 |
| Related | ND | ND | ND |
| Substances (%) | ND | ND | ND |

Ingredients corresponding to Examples 24 and 25 are tabulated in Table 54, with the amount of each ingredient given in respective percent by weight (% w/w). In each of the Examples 24 and 25, the active ingredient is marbofloxacin. In Example 24 formulations, the active strength of marbofloxacin is about 25 mg or about 50 mg or about 100 mg. In Example 25 formulations, the active strength of marbofloxacin is about 200 mg.

TABLE 54

| Ingredients | Example 24 | Example 25 |
|---|---|---|
| Granulation Aid | | |
| Mineral Oil | 7 | 7 |
| Glycerin | 16 | 17 |
| Polyethylene glycol (PEG 600) | 4.5 | 4 |
| Povidone (K-30) | 1.5 | 1 |
| Brown Iron Oxide | 0.01 | 0.01 |
| Intra-granular Ingredients | | |
| Marbofloxacin | 6.67 | 6.67 |
| Carnauba wax | 3 | 4 |
| Silicified Microcrystalline Cellulose | 22.72 | 22.72 |
| Pregelatinized starch 1500 | 3 | 3 |
| Polyethylene glycol (PEG 4000) | 5 | 2.5 |
| Calcium Sulphate dihydrate | 2 | 2 |
| Beef Flavor | 15 | 15 |
| Extra-granular Ingredients | | |
| Pregelatinized starch 1500 | 2 | 3.5 |
| Silicified Microcrystalline Cellulose | 7 | 7 |
| Beef Flavor | 3 | 3 |
| Lubrication Aid | | |
| Magnesium Stearate | 1.5 | 1.5 |
| Sodium Lauryl Sulphate | 0.1 | 0.1 |
| Total | 100 | 100 |

Procedure—Examples 24 and 25

Step 1: Intra-granular materials (marbofloxacin, carnauba wax, silicified mcc, pregelatinized starch, polyethylene glycol, calcium sulphate dehydrate and beef flavor) were passed simultaneously through #40 mesh screen and mixed together.
Step 2: Intra-granular materials (pregelatinized starch, silicified mcc and beef flavor) were passed simultaneously through #40 mesh screen, mixed together and divided into approximately two parts (75% and 25%).
Step 3: Sodium stearyl fumarate and sodium lauryl sulphate were passed through #40 mesh and mixed together.
Step 4: Povidone was added into glycerin and polyethylene glycol under continuous stirring to get clear dispersion.
Step 5: Brown iron oxide was added to dispersion from Step 4 under continuous stirring to get lump free dispersion.
Step 6: All granulation aid components except mineral oil were added to contents from Step 1 and mixed thoroughly, followed by addition of mineral oil and mixing to form and granulated wet mass.
Step 7: Wet mass from Step 6 was further passed through multi-mill using 6 mm screen.
Step 8: Approximately 75% quantity of extra-granular materials from Step 2 and milled granules from Step 7 were passed simultaneously through #8 mesh.
Step 9: Remaining quantity (25%) of extra-granular materials and granules from Step 8 were mixed together for 2 minute.
Step 10: Materials from Step 3 were added to granules from Step 9 and mixed together for 2 minute.
Step 11: Final granules were compressed on rotary tablet press using tooling. With respect to Example 24 having a 25 mg active strength, an 8.0 mm×8.0 mm rounded square shape punch was used to compress a tablet having a 375 mg fill weight. With respect to Example 24 having a 50 mg active strength, a 10.5 mm×10.5 mm rounded square shape punch was used to compress a tablet having a 750 mg fill weight. With respect to Example 24 having a 100 mg active strength, a 15.3 mm×15.3 mm rounded square shape punch was used to compress a tablet having a 1500 mg fill weight. With respect to Example 25 having a 200 mg active strength, an 18.0 mm×18.0 mm rounded square shape punch was used to compress a tablet having a 3000 mg fill weight.

Table 55: Tablet Characterization—Examples 27 and 28

TABLE 55

| Parameters | Example 24 | Example 24 | Example 24 | Example 25 |
|---|---|---|---|---|
| Active Strength | 25 mg | 50 mg | 100 mg | 200 mg |
| Weight (mg) | 375 | 750 | 1500 | 3000 |
| Shape | Rounded Square | Rounded Square | Rounded Square | Deep Rounded Square |
| Color | Light brown to brown | Light brown to brown | Light brown to brown | Light brown to brown |
| Width × Length Top (mm) | 8.0 × 8.0 | 10.5 × 10.5 | 15.3 × 15.3 | 18.0 × 18.0 |
| Width × Length Bottom (mm) | 8.0 × 8.0 | 10.5 × 10.5 | 15.3 × 15.3 | 18.0 × 18.0 |
| Thickness (mm) | 5.6 | 6.6 | 6.3 | 9.2 |
| Disintegration Time (min.) | 17 | 21 | 21 | 26 |
| Hardness (N) | 0 | 0 | 0 | 0 |
| Friability (%) | 0 | 0 | 0 | 0 |

The results of a texture analysis of the tablets formed according to Examples 24 and 25 are tabulated in Table 56. The texture analysis was performed using a CT3 Texture Analyzer (Brookfield Engineering) using a TA18 Probe and twenty-five-thousand gram (25,000 g) load cell and five gram (5 g) trigger load, over four millimeters (4 mm) using two millimeter per second (2 mm/s) test speed and using a data rate of twenty (20) points/second.

TABLE 56

| Parameters | Example 24 | Example 24 | Example 24 | Example 25 |
|---|---|---|---|---|
| Strength | 25 mg | 50 mg | 100 mg | 200 mg |
| Hardness Cycle 1 (g) | 916 | 1642 | 2062 | 2802 |
| Hardness Cycle 2 (g) | 3.8 | 254 | 146 | 274 |
| Deformation at hardness (mm) | 0.99 | 1.39 | 2.09 | 1.76 |
| Stringiness Length (mm) | 51.97 | 39.37 | 47.02 | 0 |
| Adhesiveness (mJ) | 0.1 | 0 | 0.2 | 1.7 |
| Cohesiveness | 0.14 | 0.14 | 0.1 | 0.02 |
| Gumminess (g) | 125 | 227 | 212 | 66 |
| Chewiness (mJ) | 4 | 9.3 | 17.3 | 2.3 |
| Springiness | 3.24 | 4.19 | 8.32 | 3.47 |

The results of a comparative dissolution study involving the tablets formed according to Example 24 are tabulated in Tables 57-59. The results of a comparative dissolution study involving the tablets formed according to Example 25 are tabulated in Table 60. The dissolution profiles of Examples 24 and 25 were compared to marketed products having similar active strengths using a basket apparatus rotating at 100 rpm. One-thousand milliliters (1000 ml) of 0.1 N HCl solution was used as the dissolution medium.

TABLE 57

| Time point | Marketed Product 25 mg | Example 24 25 mg |
|---|---|---|
| 0 | 0 | 0 |
| 5 | 4 | 12 |
| 15 | 42 | 53 |
| 30 | 87 | 95 |
| 45 | 101 | 101 |
| 60 | 101 | 98 |
| 90 | 102 | 101 |
| 120 | 102 | 101 |

TABLE 58

| Time point | Marketed Product 50 mg | Example 24 50 mg |
|---|---|---|
| 0 | 0 | 0 |
| 5 | 2 | 10 |
| 15 | 33 | 40 |
| 30 | 74 | 73 |
| 45 | 98 | 94 |
| 60 | 99 | 97 |
| 90 | 100 | 97 |
| 120 | 100 | 98 |

TABLE 59

| Time point | Marketed Product 100 mg | Example 24 100 mg |
|---|---|---|
| 0 | 0 | 0 |
| 5 | 1 | 7 |
| 15 | 16 | 34 |
| 30 | 48 | 63 |
| 45 | 75 | 84 |
| 60 | 93 | 98 |
| 90 | 99 | 99 |
| 120 | 99 | 99 |

TABLE 60

| Time point | Marketed Product 200 mg | Example 25 200 mg |
|---|---|---|
| 0 | 0 | 0 |
| 5 | 1 | 10 |
| 15 | 17 | 40 |
| 30 | 46 | 72 |
| 45 | 68 | 91 |
| 60 | 85 | 99 |
| 90 | 99 | 100 |
| 120 | 99 | 100 |

Tables 61-63 show the results accelerated stability study of the tablets formed according to Example 24. Table 64 shows the results accelerated stability study of the tablets formed according to Example 25. The tablets were packaged in a high-density polyethylene (HDPE) container stored at a temperature of 40. C±2. C and a relative humidity (RH) of 75%±5%.

TABLE 61

| Example 24 (25 mg) | | | |
|---|---|---|---|
| Stability Parameters | Initial | 1-Month | 3-Months |
| Loss On Drying (LOD) at 105° C. | 4.67 | 5.39 | 9.64 |
| Assay (%) | 96.3 | 97.9 | 0.95 |
| Dissolution (%) | 98 | 100 | 102 |
| Related Substances (%) | 0.69 | 0.93 | 0.81 |

TABLE 62

| Example 24 (50 mg) | | | |
|---|---|---|---|
| Stability Parameters | Initial | 1-Month | 3-Months |
| Loss On Drying (LOD) at 105° C. | 4.67 | 5.26 | 9.35 |
| Assay (%) | 97.3 | 99.7 | 96.1 |
| Dissolution (%) | 97 | 99 | 99 |
| Related Substances (%) | 0.49 | 0.76 | 0.82 |

TABLE 63

| Example 24 (100 mg) | | | |
|---|---|---|---|
| Stability Parameters | Initial | 1-Month | 3-Months |
| Loss On Drying (LOD) at 105° C. | 4.56 | 6.01 | 9.51 |
| Assay (%) | 101.6 | 102.7 | 98.1 |
| Dissolution (%) | 98 | 99 | 98 |
| Related Substances (%) | 0.55 | 0.8 | 0.58 |

TABLE 64

| Example 24 (200 mg) | | | |
|---|---|---|---|
| Stability Parameters | Initial | 1-Month | 3-Months |
| Loss On Drying (LOD) at 105° C. | 5.45 | 5.61 | 8.09 |
| Assay (%) | 102.7 | 99.1 | 101.7 |
| Dissolution (%) | 99 | 95 | 98 |
| Related Substances (%) | 0.47 | 0.37 | 0.32 |

Ingredients corresponding to Examples 26-28 are tabulated in Table 65, with the amount of each ingredient given in respective percent by weight (% w/w). In each of the Examples 26-28, the active ingredient is pimobendan. In each of the Examples 26-28, the active strength of pimobendan is about 10 mg.

TABLE 65

| Ingredients | Example 26 | Example 27 | Example 28 |
|---|---|---|---|
| Granulation Aid Ingredients | | | |
| Soybean Oil | 8 | 8 | — |
| Mineral Oil | — | — | 4.71 |
| BHA (Butylated Hydroxyanisole) | 0.02 | 0.02 | — |
| BHT (Butylated Hydroxytoluene) | 0.08 | 0.08 | — |
| Polyethylene glycol (PEG 600) | — | — | 2.83 |
| Polysorbate 80 | — | — | 2.83 |

TABLE 65-continued

| Ingredients | Example 26 | Example 27 | Example 28 |
|---|---|---|---|
| Tartaric Acid | — | — | 4.72 |
| Glycerin | — | — | 17.32 |
| Pimobendan | 0.33 | 0.33 | 0.33 |
| Cremophor | 5 | 3 | — |
| Citric Acid | — | 8 | — |
| Sorbitol | 16 | 11 | — |
| Povidone (K-30) | 0.2 | 0.2 | 0.19 |
| Brown Iron Oxide | 0.01 | 0.01 | 0.01 |
| Intra-granular Ingredients | | | |
| Carnauba wax | 5 | 5 | 4.72 |
| Sodium Lauryl Sulphate | 1 | — | — |
| Mannitol | 12.76 | — | — |
| Lactose Monohydrate | — | 6 | 3.5 |
| Pregelatinized Starch | — | — | 2 |
| Soluplus | 5 | 5 | 4.72 |
| Silicified Microcrystalline Cellulose | — | 14.76 | 13.72 |
| Calcium Sulfate Dihydrate | 2 | 2 | 2 |
| Beef Flavor | 15 | 15 | 15 |
| Calcium Carboxymethyl cellulose (ECG 505) | 5.5 | — | 5 |
| Croscarmellose Sodium | 6 | 4.5 | — |
| Extra-granular Ingredients | | | |
| Calcium Carboxymethyl cellulose (ECG 505) | 5.5 | 1.6 | 3 |
| Silicified Microcrystalline Cellulose | 2 | 2.5 | 2 |
| Beef Flavor | 3 | 3 | 3 |
| Croscarmellose Sodium | 4.5 | 6 | 4.7 |
| Lactose Monohydrate (Supertab 14 SD) | — | — | 1.7 |
| Lactose Monohydrate (Granulac 200) | 2 | 2 | — |
| Flow Aid Ingredients | | | |
| Magnesium Stearate | 1 | — | — |
| Sodium Lauryl Sulphate | 0.1 | — | — |
| Sodium Stearyl Fumarate | — | 2 | 2 |
| Total | 100 | 100 | 100 |

Procedure—Example 26

Step 1: pimobendan was added in cremophor under continuous stirring to achieve homogenous dispersion Step 2: BHA and BHT were added to soybean oil, mixed thoroughly and added to contents from Step 1.

Step 3: In separate vessel povidone was added to sorbitol under continuous stirring to form clear dispersion followed by addition of brown iron oxide under continuous stirring to form lump free dispersion.

Step 4: Intra-granular materials (sodium lauryl sulphate, carnauba wax, mannitol, soluplus, calcium carboxymethyl cellulose, calcium sulphate dihydrate, beef flavor and croscarmellose sodium) were passed simultaneously through #40 mesh screen and again were passed through #40 mesh screen and mixed together for ten minutes.

Step 5: Extra-granular materials (calcium carboxymethyl cellulose, silicified microcrystalline cellulose, lactose monohydrate, beef flavor and croscarmellose sodium) were passed simultaneously through #40 mesh screen and once gain were passed through #40 mesh screen and mixed together and further divided to two equal parts.

Step 6: Magnesium stearate and sodium lauryl sulphate were passed through #40 mesh screen.

Step 7: Granulation aid components were added to materials from Step 4 and mixed thoroughly followed by kneading for about two (2) minutes.

Step 8: Wet mass from Step 7 was passed through cone mill using six millimeter (6 mm) screen to form granules.

Step 9: Approximately 50% quantity of extra-granular materials from Step 5 and milled granules of Step 8 were passed through #8 mesh screen.

Step 10: Remaining quantity of extra-granular materials (50%) of Step 5 were mixed with granules from Step 9 and mixed together for two (2) minutes.

Step 11: Materials from Step 6 were further added to granules from Step 12 and mixed together for two (2) minutes.

Step 12: Using final granules from Step 11 compression was performed using rotary tablet press using 18.0 mm×18.0 mm rounded square shape punch.

Procedure—Example 27

Step 1: Pimobendan was added in cremophor under continuous stirring to achieve homogenous dispersion Step 2: BHA and BHT were added to soybean oil, mixed thoroughly and added to contents from Step 1.

Step 3: In separate vessel citric acid was added to sorbitol under continuous stirring to form clear dispersion.

Step 4: Povidone was added to dispersion from Step 3 under continuous stirring to form clear dispersion.

Step 5: Brown iron oxide was added to dispersion from Step 4 under continuous stirring to form uniform dispersion.

Step 6: Intra-granular materials (carnauba wax, lactose monohydrate, soluplus, silicified microcrystalline cellulose, calcium sulphate dihydrate, beef flavor and croscarmellose sodium) were passed simultaneously through #40 mesh screen followed by passing again through #40 mesh and mixing together for ten minutes.

Step 7: Extra-granular material (calcium carboxymethyl cellulose, silicified microcrystalline cellulose, lactose monohydrate, beef flavor and croscarmellose sodium) were passed through #40 mesh screen and followed by passing again through #40 mesh and mixing together and were divided further to two equal parts.

Step 8: Sodium stearyl fumarate was passed through #40 mesh screen.

Step 9: Granulation aid components were added to the materials from Step 6 and mixed thoroughly followed by kneading for about two (2) minutes to form wet mass.

Step 10: Wet mass from Step 9 was passed through cone mill using six millimeter (6 mm) screen to form granules.

Step 11: Approximately 50% quantity of extra-granular materials from Step 7 and milled granules of Step 10 were passed simultaneously through #8 mesh screen.

Step 12: Remaining quantity of extra-granular materials (50%) from Step 7 were mixed with granules from Step 11 and mixed together for two (2) minutes.

Step 13: Material from Step 8 was added to granules from Step 12 and mixed together for two (2) minutes.

Step 14: Granules from Step 13 were used for compression using rotary tablet press using 18.0 mm×18.0 mm rounded square shape punch.

Procedure—Example 28

Step 1: Intra-granular materials (carnauba wax, lactose monohydrate, soluplus, silicified microcrystalline cellulose, calcium sulphate dihydrate, beef flavor, calcium carboxymethyl cellulose and croscarmellose sodium) were passed simultaneously through #40 mesh screens and passed again through #40 mesh screen followed by mixing together for ten minutes.

Step 2: Extra-granular materials (calcium carboxymethyl cellulose, silicified microcrystalline cellulose, lactose monohydrate, beef flavor and croscarmellose sodium) were passed through #40 mesh screen simultaneously and passed again through #40 mesh screen followed by mixing together and further approximately dividing to two parts (75% and 25%).

Step 3: Sodium stearyl fumarate was sifted through #40 mesh screen.

Step 4: Glycerin and polyethylene glycol kept in a vessel under stirring.

Step 5: Tartaric acid was added to materials from Step 4 under continuous stirring to get a lump free dispersion.

Step 6: Povidone was added into dispersion from Step 5 under continuous stirring to obtain a clear, lump free dispersion.

Step 7: Brown iron oxide was added into contents from Step 6 under continuous stirring to obtain a lump free dispersion.

Step 8: Pimobendan was added in polysorbate 80 under continuous stirring.

Step 9: Mineral Oil was added to material from Step 8 under continuous stirring to form a dispersion.

Step 10: Granulation aid components were added to the materials from Step 1 and mixed thoroughly followed by kneading for two (2) minutes to form wet mass.

Step 11: Wet mass from Step 10 and 75% extra-granular materials from Step 2 were passed simultaneously through cone-mill using six millimeter (6 mm) screen at slow speed and knife forward to form granules.

Step 12: Granules from Step 11 and remaining 25% extra-granular materials from Step 2 were passed through #8 mesh granules.

Step 13: Granules from Step 12 were mixed together with materials from Step 3 for about five (5) minutes.

Step 14: Final granules were compressed using rotary tablet press using 18.0 mm×18.0 mm rounded square shape punch.

Table 66: Tablet Characterization—Examples 26-28

TABLE 66

| Parameters | Example 26 | Example 27 | Example 28 |
|---|---|---|---|
| Weight (mg) | 3000 | 3000 | 3000 |
| Shape | Rounded Square | Rounded Square | Rounded Square |
| Color | Light brown to brown | Light brown to brown | Light brown to brown |
| Width × Length Top (mm) | 18.0 × 18.0 | 18.0 × 18.0 | 18.0 × 18.0 |
| Width × Length Bottom (mm) | 18.0 × 18.0 | 18.0 × 18.0 | 18.0 × 18.0 |
| Thickness (mm) | 9.1 | 9.4 | 8.8 |
| Disintegration Time (min.) | 6 min | 7 min | 8 min |
| Hardness (N) | 30 | 25 | 0 |
| Friability (%) | 0 | 0 | 0 |

The results of a texture analysis of the tablets formed according to Example 28 are tabulated in Table 67. The texture analysis was performed using a CT3 Texture Analyzer (Brookfield Engineering) using a TA18 Probe and twenty-five-thousand gram (25,000 g) load cell and five gram (5 g) trigger load, over four millimeters (4 mm) using two millimeter per second (2 mm/s) test speed and using a data rate of twenty (20) points/second.

TABLE 67

| Parameters | Example 28 |
|---|---|
| Hardness Cycle 1 (g) | 888 |
| Hardness Cycle 2 (g) | 132 |
| Deformation at hardness (mm) | 1.58 |
| Stringiness Length (mm) | 0.1 |
| Adhesiveness (mJ) | 0.1 |
| Cohesiveness | 0.04 |
| Gumminess (g) | 33 |
| Chewiness (mJ) | 1.5 |
| Springiness | 4.59 |

The results of a comparative dissolution study involving the tablets formed according to Examples 26-28 are tabulated in Tables 68-70, respectively. The dissolution profiles of Examples 26-28 were compared to a marketed products having similar active strengths. A paddle apparatus rotating at 50 rpm. Nine-hundred milliliters (900 ml) of 0.1 N HCl solution was used as the dissolution medium.

TABLE 68

| Time point | Marketed Product | Example 26 |
|---|---|---|
| 0 | 0 | 0 |
| 5 | 26 | 15 |
| 10 | 48 | 29 |
| 15 | 67 | 36 |
| 30 | 92 | 55 |
| 45 | 97 | 65 |
| 60 | 98 | 67 |
| 90 | 97 | 71 |

TABLE 69

| Time point | Marketed Product | Example 27 |
|---|---|---|
| 0 | 0 | 0 |
| 5 | 26 | 25 |
| 10 | 48 | 44 |
| 15 | 67 | 59 |
| 30 | 92 | 80 |
| 45 | 97 | 91 |
| 60 | 98 | 94 |
| 90 | 97 | 96 |

TABLE 70

| Time point | Marketed Product | Example 28 |
|---|---|---|
| 0 | 0 | 0 |
| 5 | 26 | 31 |
| 10 | 48 | 51 |
| 15 | 67 | 64 |
| 30 | 92 | 83 |
| 45 | 97 | 92 |
| 60 | 98 | 96 |
| 90 | 97 | 97 |

Ingredients corresponding to Example 29 are tabulated in Table 71, with the amount of each ingredient given in respective percent by weight (% w/w). The active ingredient in Example 29 is ibuprofen. Ibuprofen particles are coated with hydrophilic hydrogel coating creating effective taste barrier. In Example 29, the active strength of ibuprofen is about 200 mg per unit. Because ibuprofen in Example 29 is coated with hydrophilic hydrogel coating, it has an average assay of about ninety-two (92) percent by weight (% w/w). That is, about 217.4 mg per unit of ibuprofen coated with hydrophilic hydrogel coating is incorporated to composition of Example 29.

TABLE 71

| Ingredients | Example 29 |
|---|---|
| Granulation Aid Ingredients | |
| Soybean Oil | 9.42 |
| Zea Mays Oil & BHA & BHT | 0.10 |
| Sorbitol | 14.42 |
| Polyethylene glycol (PEG 400) | 5.77 |
| Povidone K30 | 1.92 |
| Liquid Strawberry Flavor | 0.58 |
| Intra-granular Ingredients | |
| Carnauba Wax | 4.81 |
| Hydrophilic hydrogel coated Ibuprofen | 8.36 |
| Silicified Microcrystalline Cellulose | 15.38 |
| Lactose Monohydrate | 3.85 |
| Sucralose | 0.19 |
| Pregelatinized Corn Starch | 6.75 |
| Croscarmellose Sodium | 2.88 |
| Xylitol | 4.81 |
| Extra-granular Ingredients | |
| Pregelatinized Corn Starch | 6.06 |
| Sucralose | 0.19 |
| Silicified Microcrystalline Cellulose | 4.81 |
| Xylitol | 2.88 |
| Lactose Monohydrate | 4.81 |
| Flow Aid Ingredients | |
| Magnesium Stearate | 1.00 |
| Colloidal Silicon Dioxide | 1.00 |
| Total | 100 |

Procedure—Examples 29

Step 1: Intra-granular materials (hydrogel coated ibuprofen, carnauba wax, silicified mcc, pregelatinized starch, lactose monohydrate, sucralose, croscarmellose sodium and xylitol) were passed simultaneously through #30 mesh screen and mixed together.
Step 2: Extra-granular materials (pregelatinized starch, silicified mcc, xylitol and lactose monohydrate) were passed simultaneously through #30 mesh screen, mixed together and divided into approximately two parts (75% and 25%).
Step 3: magnesium stearate and colloidal silicon dioxide were mixed together and passed together through #30 mesh screen.
Step 4: Povidone was added into glycerin and polyethylene glycol under continuous stirring to get clear dispersion.
Step 5: Liquid Strawberry Flavor was added to dispersion from Step 4 under continuous stirring to get lump free dispersion.
Step 6: *Zea mays* oil and BHA and BHT was added to soybean oil under continuous stirring to get clear dispersion.
Step 7: All granulation aid components except mixture of soybean oil and *Zea mays* oil and BHA and BHT and were added to contents from Step 1 and mixed thoroughly, followed by addition of mixture of soybean oil and *Zea mays* oil and BHA and BHT and mixing to form and granulated wet mass.
Step 8: Wet mass from Step 7 was further passed through multi-mill using 6 mm screen.
Step 9: Approximately 75% quantity of extra-granular materials from Step 2 and milled granules from Step 8 were passed simultaneously through #8 mesh.
Step 10: Remaining quantity (25%) of extra-granular materials and granules from Step 9 were mixed together for 2 minute.
Step 11: Materials from Step 3 were added to granules from Step 10 and mixed together for 2 minute.
Step 12: Final granules were compressed on rotary tablet press using tooling using an 18.0 mm×18.0 mm rounded square shape punch was used to compress a tablet having a 2600 mg fill weight.
Table 72: Tablet Characterization—Example 29

TABLE 72

| Parameters | Example 29 |
|---|---|
| Active Strength | 200 mg |
| Weight (mg) | 2600 |
| Shape | Rounded Square |
| Color | white to off white |
| Width × Length Top (mm) | 18.0 × 18.0 |
| Width × Length Bottom (mm) | 18.0 × 18.0 |
| Thickness (mm) | 7.0 |
| Disintegration Time (min.) | 07 |
| Hardness (N) | 0 |
| Friability (%) | 0.2 |

Ingredients corresponding to Example 30 are tabulated in Table 73, with the amount of each ingredient given in respective percent by weight (% w/w). The active ingredient in Example 30 is acetaminophen. Acetaminophen particles are coated with hydrophilic hydrogel coating creating effective taste barrier. In Example 30 formulation, the active strength of acetaminophen is about 160 mg per unit. Because acetaminophen in Example 30 is coated with hydrophilic hydrogel coating, it has an average assay of about ninety-two (92) percent by weight (% w/w). That is, about 174 mg per unit of ibuprofen coated with hydrophilic hydrogel coating is incorporated to composition of Example 30.

TABLE 73

| Ingredients | Example 30 |
|---|---|
| Granulation Aid Ingredients | |
| Mineral Oil | 9.60 |
| Sorbitol | 15.00 |
| Polyethylene glycol (PEG 400) | 6.00 |
| Povidone K30 | 2.00 |
| Liquid Strawberry Flavor | 0.60 |
| Intra-granular Ingredients | |
| Carnauba Wax | 5.00 |
| Hydrophilic Hydrogel Coated Acetaminophen | 6.96 |

TABLE 73-continued

| Ingredients | Example 30 |
| --- | --- |
| Silicified Microcrystalline Cellulose | 16.00 |
| Lactose Monohydrate | 4.00 |
| Sucralose | 0.20 |
| Pregelatinized Corn Starch | 5.04 |
| Croscarmellose Sodium | 3.04 |
| Xylitol | 5.00 |
| Extra-granular Ingredients | |
| Pregelatinized Corn Starch | 6.32 |
| Sucralose | 0.20 |
| Silicified Microcrystalline Cellulose | 5.04 |
| Xylitol | 3.00 |
| Lactose Monohydrate | 5.00 |
| Flow Aid Ingredients | |
| Magnesium Stearate | 1.00 |
| Colloidal Silicon Dioxide | 1.00 |
| Total | 100 |

Procedure—Examples 30

Step 1: Intra-granular materials (hydrogel coated ibuprofen, carnauba wax, silicified mcc, pregelatinized starch, lactose monohydrate, sucralose, croscarmellose sodium and xylitol) were passed simultaneously through #30 mesh screen and mixed together.

Step 2: Extra-granular materials (pregelatinized starch, silicified mcc, xylitol and lactose monohydrate) were passed simultaneously through #30 mesh screen, mixed together and divided into approximately two parts (75% and 25%).

Step 3: Magnesium stearate and colloidal silicon dioxide were mixed together and passed together through #30 mesh screen.

Step 4: Povidone was added into glycerin and polyethylene glycol under continuous stirring to get clear dispersion.

Step 5: Liquid strawberry flavor was added to dispersion from Step 4 under continuous stirring to get lump free dispersion.

Step 6: All granulation aid components except mineral oil were added to contents from Step 1 and mixed thoroughly, followed by addition of mineral oil and mixing to form and granulated wet mass.

Step 7: Wet mass from Step 6 was further passed through multi-mill using 6 mm screen.

Step 8: Approximately 75% quantity of extra-granular materials from Step 2 and milled granules from Step 7 were passed simultaneously through #8 mesh.

Step 9: Remaining quantity (25%) of extra-granular materials and granules from Step 8 were mixed together for 2 minutes.

Step 10: Materials from Step 3 were added to granules from Step 9 and mixed together for 2 minutes.

Step 11: Final granules were compressed on rotary tablet press using tooling using an 18.0 mm×18.0 mm rounded square shape punch was used to compress a tablet having a 2500 mg fill weight.

Table 74: Tablet Characterization—Example 30

TABLE 74

| Parameters | Example 30 |
| --- | --- |
| Active Strength | 200 mg |
| Weight (mg) | 2500 |
| Shape | Rounded Square |
| Color | white to off white |
| Width × Length Top (mm) | 18.0 × 18.0 |
| Width × Length Bottom (mm) | 18.0 × 18.0 |
| Thickness (mm) | 6.7 |
| Disintegration Time (min.) | 08 |
| Hardness (N) | 0 |
| Friability (%) | 0.2 |

The preferred forms of the invention described above are to be used as illustration only and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and access the reasonably fair scope of the present invention as pertains to any apparatus not materially departing from but outside the literal scope of the invention set forth in the following claims.

What is claimed is:

1. A process for manufacture of an edible, soft-chew, semi-plastic tablet unit dosage form for the oral administration of an active ingredient comprising the steps of:
    (a) combining a plurality of ingredients to form a mixture; said ingredients comprising:
        said active ingredient in a concentration ranging from 0.1% w/w to 20% w/w, polyethylene glycol in a concentration ranging from 0.1% w/w to 12% w/w, povidone in a concentration ranging from 0.1% w/w to 3% w/w, and microcrystalline cellulose in a concentration ranging from 0.1% w/w to 35% w/w;
    (b) sifting said mixture to form granules;
    (c) compressing said granules using a tablet press to form said tablet,
    wherein said tablet has:
        a hardness of less than 2 kp when measured on a tablet hardness tester;
        a friability of less than 1% at 100 rotations when tested in accordance with United States Pharmacopeia test <1216>;
        a water content ranging from 4% w/w to 15% w/w of total weight of the tablet; and
        a disintegration time of less than 60-minutes when measured in accordance with United States Pharmacopeia test <701>,
    wherein said process does not include a heating step,
    wherein said tablet is formed without molding or extrusion.

2. The process as claimed in claim 1, wherein said tablet has a disintegration time in the range of about 3-minutes to about 60-minutes when measured in accordance with United States Pharmacopeia test <701>.

3. The process as claimed in claim 1, wherein said tablet has a normalized hardness of less than about 0.2 kp/cm$^2$.

4. The process as claimed in claim 1, said plurality of ingredients further comprising:
   croscarmellose sodium in a concentration ranging from 0.1% w/w to 15% w/w.

5. The process as claimed in claim 1, said plurality of ingredients further comprising:
   corn starch in a concentration ranging from 0.1% w/w to 16% w/w.

6. The process as claimed in claim 1, said plurality of ingredients further comprising:
   lactose in a concentration ranging from 0.1% w/w to 30% w/w.

7. The process as claimed in claim 1, said plurality of ingredients further comprising:
   carnauba wax in a concentration ranging from 0.1% w/w to 8% w/w.

8. The process as claimed in claim 1, said plurality of ingredients further comprising:
   mineral oil in a concentration ranging from 0.1% w/w to 12% w/w.

\* \* \* \* \*